US011579336B2

(12) United States Patent
Topolancik et al.

(10) Patent No.: US 11,579,336 B2
(45) Date of Patent: Feb. 14, 2023

(54) PHOTONIC STRUCTURE-BASED DEVICES AND COMPOSITIONS FOR USE IN LUMINESCENT IMAGING OF MULTIPLE SITES WITHIN A PIXEL, AND METHODS OF USING THE SAME

(71) Applicant: ILLUMINA, INC., San Diego, CA (US)

(72) Inventors: Juraj Topolancik, Redwood City, CA (US); Cheng Frank Zhong, San Francisco, CA (US)

(73) Assignee: Illumina, Inc., San Diego, CA (US)

( * ) Notice: Subject to any disclaimer, the term of this patent is extended or adjusted under 35 U.S.C. 154(b) by 125 days.

(21) Appl. No.: 16/093,070

(22) PCT Filed: Apr. 21, 2017

(86) PCT No.: PCT/US2017/028883
§ 371 (c)(1),
(2) Date: Oct. 11, 2018

(87) PCT Pub. No.: WO2017/184997
PCT Pub. Date: Oct. 26, 2017

(65) Prior Publication Data
US 2019/0170904 A1 Jun. 6, 2019

Related U.S. Application Data

(60) Provisional application No. 62/326,568, filed on Apr. 22, 2016.

(51) Int. Cl.
*H01L 27/146* (2006.01)
*G02B 1/00* (2006.01)
(Continued)

(52) U.S. Cl.
CPC .............. *G02B 1/005* (2013.01); *B82Y 20/00* (2013.01); *G01N 21/6454* (2013.01);
(Continued)

(58) Field of Classification Search
None
See application file for complete search history.

(56) References Cited

U.S. PATENT DOCUMENTS 7,057,026 B2  6/2006 Barnes et al.
7,211,414 B2  5/2007 Hardin et al.
(Continued)

FOREIGN PATENT DOCUMENTS

CN  101868727  10/2010
CN  104568850   4/2015
(Continued)

OTHER PUBLICATIONS

Altug et al., "Polarization control and sensing with twodimensional coupled photonic crystal microcavity arrays," Opt. Lett. 30: 1422-1428 (2011).
(Continued)

*Primary Examiner* — Neil N Turk
(74) *Attorney, Agent, or Firm* — Snell & Wilmer, L.L.P.; Jaime D. Choi; Glen K Thurston

(57) ABSTRACT

A device for luminescent imaging includes an array of imaging pixels, a photonic structure over the array of imaging pixels, and an array of features over the photonic structure. A first feature of the array of features is over a first pixel of the array of imaging pixels, and a second feature of the array of features is over the first pixel and spatially displaced from the first feature. A first luminophore is within or over the first feature, and a second luminophore is within or over the second feature. The device includes a radiation source to generate first photons having a first characteristic
(Continued)

at a first time, and generate second photons having a second characteristic at a second time. The first pixel selectively receives luminescence emitted by the first and second luminophores responsive to the first photons at the first time and second photons at the second time, respectively.

25 Claims, 10 Drawing Sheets

(51) Int. Cl.
   *G02B 1/02* (2006.01)
   *G01N 21/64* (2006.01)
   *B82Y 20/00* (2011.01)

(52) U.S. Cl.
   CPC ..... *G01N 21/6456* (2013.01); *G01N 21/6458* (2013.01); *G02B 1/02* (2013.01); *H01L 27/14601* (2013.01); *H01L 27/14603* (2013.01)

(56) References Cited

U.S. PATENT DOCUMENTS

| | | | |
|---|---|---|---|
| 7,315,019 | B2 | 1/2008 | Turner et al. |
| 7,329,492 | B2 | 2/2008 | Hardin et al. |
| 7,405,281 | B2 | 6/2008 | Xu et al. |
| 7,768,640 | B2 | 8/2010 | Cunningham et al. |
| 8,344,333 | B2 | 1/2013 | Lu et al. |
| 2003/0219754 | A1* | 11/2003 | Oleksy ............... G01N 21/6428 435/6.12 |
| 2006/0006485 | A1 | 1/2006 | Mouli |
| 2007/0087382 | A1* | 4/2007 | Howorka ............... B82Y 30/00 435/7.1 |
| 2008/0014632 | A1* | 1/2008 | Cunningham ....... G01N 33/552 435/288.7 |
| 2008/0108082 | A1 | 5/2008 | Rank et al. |
| 2008/0278722 | A1 | 11/2008 | Cunningham et al. |
| 2010/0247382 | A1 | 9/2010 | Lee |
| 2011/0059865 | A1 | 3/2011 | Smith et al. |
| 2013/0004954 | A1 | 1/2013 | Bianchessi et al. |
| 2013/0079232 | A1 | 3/2013 | Kain et al. |
| 2014/0079923 | A1 | 3/2014 | George et al. |
| 2014/0243224 | A1 | 8/2014 | Barnard et al. |
| 2014/0274746 | A1 | 9/2014 | Khurana et al. |
| 2015/0184237 | A1* | 7/2015 | Su .......................... G01N 27/00 435/6.1 |
| 2015/0268157 | A1 | 9/2015 | Hyde et al. |
| 2016/0041095 | A1* | 2/2016 | Rothberg ............. C12Q 1/6874 506/4 |
| 2016/0047747 | A1 | 2/2016 | Lafferty et al. |
| 2017/0191125 | A1* | 7/2017 | Vijayan ................ G01N 21/554 |
| 2017/0275690 | A1* | 9/2017 | Dehlinger .......... G01N 21/6428 |

FOREIGN PATENT DOCUMENTS

| | | |
|---|---|---|
| JP | 2003177097 | 6/2003 |
| JP | 2005508495 | 3/2005 |
| JP | 2005099007 | 4/2005 |
| JP | 2007501391 | 1/2007 |
| JP | 2008076407 A | 4/2008 |
| JP | 2009503442 A | 1/2009 |
| JP | 2011504595 | 2/2011 |
| JP | 2012515930 A | 7/2012 |
| JP | 2012145939 A | 8/2012 |
| JP | 2013524174 A | 6/2013 |
| JP | 2013545127 A | 12/2013 |
| JP | 2016537999 A | 12/2016 |
| JP | 2017502310 A | 1/2017 |
| JP | 2017525958 A | 9/2017 |
| JP | 2017531168 A | 10/2017 |
| WO | WO 1991006678 | 5/1991 |
| WO | WO 20040018497 | 3/2004 |
| WO | WO 20070123744 | 11/2007 |
| WO | 2015074004 A1 | 5/2015 |
| WO | WO 2015074005 | 5/2015 |
| WO | 2016/023010 | 2/2016 |
| WO | WO 2016023011 | 2/2016 |

OTHER PUBLICATIONS

Regmi et al., "Nanoscale volume confinement and fluorescence enhancement with double nanohole aperture," Scientific Reports 5: 15852-1-5 (2015).
Estrada et al., "Small volume excitation and enhancement of dye fluorescence on a 2D photonic crystal surface," Opt. Express 18: 3693-3699 (2010).
Zhen et al., "Enabling enhanced emission and low-threshold lasing of organic molecules using special Fano resonances of macroscopic photonic crystals," PNAS 110: 13711-13716 (2013).
Kaji et al., "Fabrication of two-dimensional Ta2O5 photonic crystal slabs with ultra-low background emission toward highly sensitive fluorescence spectroscopy," Opt. Express 19: 1422-1428 (2011).
Pokhriyal et al., "Photonic crystal enhanced fluorescence using a quartz substrate to reduce limits of detection," Opt. Express 18: 24793-24808 (2010).
Hahn et al., "Laser scanning lithography for surface micropatteming on hydrogels," Adv. Mater. 17: 2939-2942 (2005).
Brakenhoff et al., "Confocal light scanning microscopy with high-apertur immersion lenses," J. Microsc. 117:219-232 (1997).
Van Wolferen et al., "Laser interference lithography," in Lithography: Principles, Processes and Materials, pp. 133-148, Theodore Hennessy, Ed., Nova Science Publishers, Inc. (2011).
He et al., "Polarization control in flexible interference lithography for nano-patterning of different photonic structures with optimized contrast," Optics Express 11518-11525 (May 4, 2015).
Bentley et al., "Accurate whole human genome sequencing using reversible terminator chemistry", Nature 456:53-59 (2008).
Written Opinion and International Search Report, PCT/US2017/028883, filed Apr. 21, 2017, dated Sep. 22, 2017.
First Office Action, CN Application No. 201780039083, filed Apr. 21, 2017, dated Apr. 1, 2020.
Supplementary Search, CN Application No. 201780039083, filed Apr. 21, 2017, dated Nov. 11, 2020.
First Search, CN Application No. 201780039083, filed Apr. 21, 2017, dated Mar. 23, 2020.
Decision on Granting, RU Application No. 2018140124/28, filed Apr. 21, 2017, dated Jul. 14, 2020.

* cited by examiner

1 Site/Pixel

1 NW per Pixel

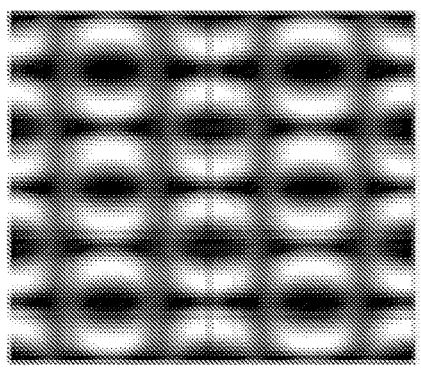
FIG. 6B
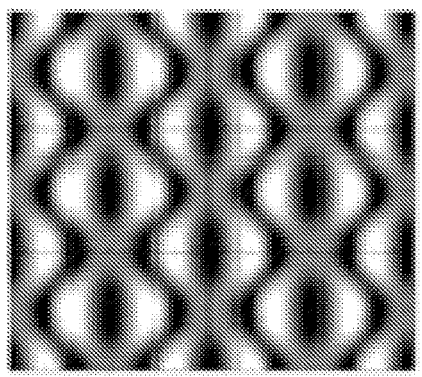
FIG. 6A
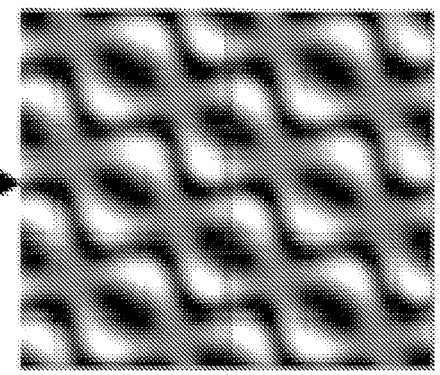
FIG. 6D
FIG. 6C
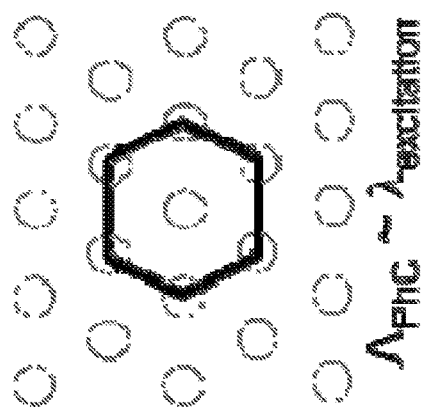
FIG. 5

FIG. 7A 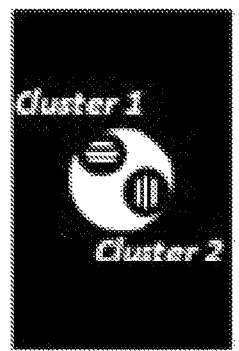 FIG. 7D 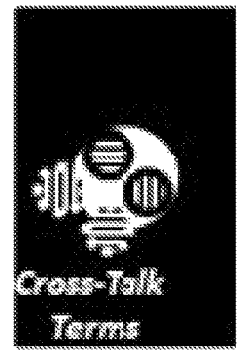
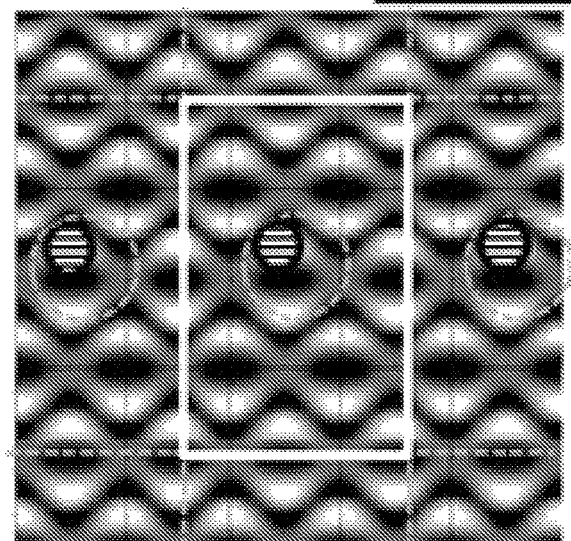
↕ *Y-Polarization*
FIG. 7B
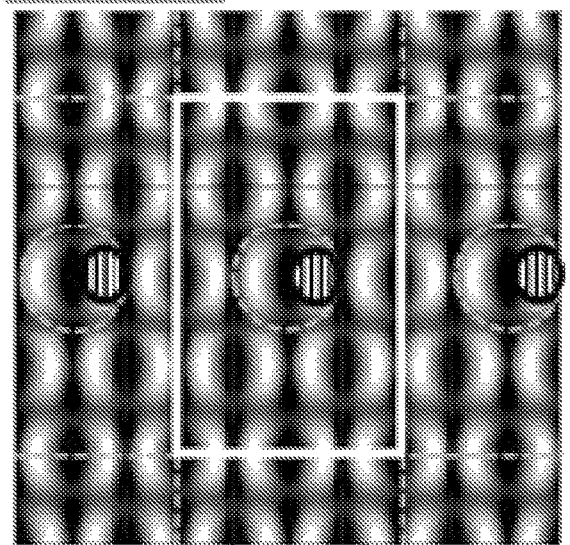
↔ *X-Polarization*
FIG. 7C

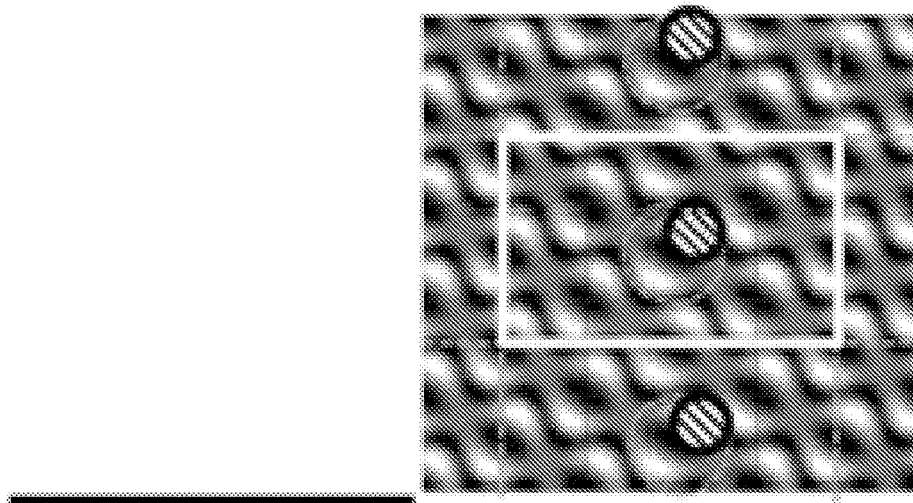
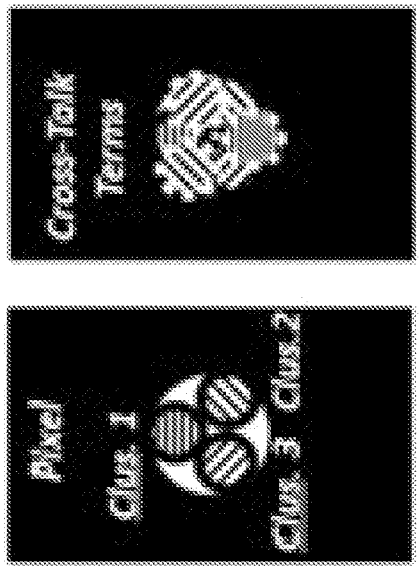
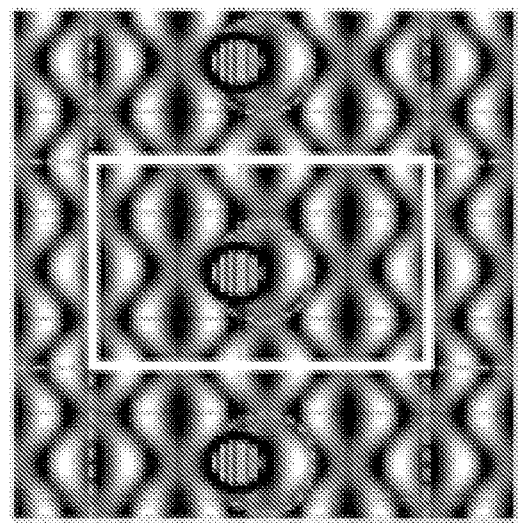
FIG. 8A  FIG. 8E
FIG. 8D
FIG. 8C
FIG. 8B

PHOTONIC STRUCTURE-BASED DEVICES AND COMPOSITIONS FOR USE IN LUMINESCENT IMAGING OF MULTIPLE SITES WITHIN A PIXEL, AND METHODS OF USING THE SAME

CROSS-REFERENCE TO RELATED APPLICATIONS

This application is a 35 U.S.C. § 371 National Stage application of International Patent Application No. PCT/US2017/028883, filed on Apr. 21, 2017, which claims the benefit of U.S. Provisional Patent Application No. 62/326,568, filed Apr. 22, 2016 and entitled "PHOTONIC STRUCTURE-BASED DEVICES AND COMPOSITIONS FOR USE IN LUMINESCENT IMAGING OF MULTIPLE SITES WITHIN A PIXEL, AND METHODS OF USING THE SAME;" each of the aforementioned applications is incorporated by reference in its entirety.

FIELD

This application generally relates to luminescent imaging.

BACKGROUND

Certain state-of-the-art sequencing tools developed by industry leaders rely on various "sequencing by synthesis (SBS)" chemistries to determine a polynucleotide sequence, such as a DNA or RNA sequence. Sequencing can involve using luminescent imaging, such as a fluorescent microscopy system, to identify nucleotides or localized clusters of identical nucleotides by emission wavelength of their respective fluorescent markers. Although some SBS chemistries under development can require as few as a single dye, multiple fluorescent dyes (up to four) are generally used in commercial systems so as to uniquely identify the nucleotides in a polynucleotide, such as A, G, C, and T nucleotides in DNA.

SUMMARY

Embodiments of the present invention provide photonic structure-based devices and compositions for use in luminescent imaging of multiple sites within a pixel, and methods of using the same.

Under one aspect, a device is provided for use in luminescent imaging. The device can include an array of imaging pixels, and a photonic structure disposed over the array of imaging pixels. The device further can include an array of features disposed over the photonic structure. A first feature of the array of features can be disposed over a first pixel of the array of imaging pixels, and a second feature of the array of features can be disposed over the first pixel and spatially displaced from the first feature. A first luminophore can be disposed within or over the first feature, and a second luminophore can be disposed within or over the second feature. The device further can include a radiation source configured to generate first photons having a first characteristic at a first time, and configured to generate second photons having a second characteristic at a second time. The second characteristic can be different than the first characteristic, and the second time can be different than the first time. The first pixel can selectively receive luminescence emitted by the first luminophore responsive to the first photons at the first time, and can selectively receive luminescence emitted by the second luminophore responsive to the second photons at the second time.

Optionally, the first photons having the first characteristic generate a first resonant pattern within the photonic structure at the first time, the first resonant pattern selectively exciting the first luminophore relative to the second luminophore. Optionally, the second photons having the second characteristic generate a second resonant pattern within the photonic structure at the second time, the second resonant pattern selectively exciting the second luminophore relative to the first luminophore.

Additionally, or alternatively, the array of imaging pixels, the photonic structure, and the array of features optionally are monolithically integrated with one another.

Additionally, or alternatively, the photonic structure optionally includes a photonic crystal, a photonic superlattice, a microcavity array, or an array of plasmonic nanoantennas.

Additionally, or alternatively, the array of features optionally includes a plurality of wells. The first feature can include a first well within which the first luminophore is disposed, and the second feature can include a second well within which the second luminophore is disposed. Alternatively, the array of features optionally includes a plurality of posts. The first feature can include a first post upon which the first luminophore is disposed, and the second feature can include a second post upon which the second luminophore is disposed.

Additionally, or alternatively, the first and second characteristics optionally are selected independently from the group consisting of wavelength, polarization, and angle. For example, the first characteristic optionally includes a first linear polarization, and the second characteristic optionally includes a second linear polarization that is different than the first linear polarization. Optionally, the first linear polarization is substantially orthogonal to the second linear polarization, or optionally the first linear polarization is rotated relative to the second linear polarization by between about 15 degrees and about 75 degrees. Additionally, or alternatively, the first characteristic optionally can include a first wavelength, and the second characteristic optionally can include a second wavelength that is different than the first wavelength.

Additionally, or alternatively, the radiation source optionally includes an optical component. Optionally, the device further includes a controller coupled to the optical component and configured to control the optical component so as to impose the first characteristic on the first photons and configured to impose the second characteristic on the second photons. Optionally, the optical component includes a birefringent material configured to rotate the first photons to a first linear polarization responsive to a first control signal by the controller, and configured to rotate the second photons to a second linear polarization responsive to a second control signal by the controller.

Additionally, or alternatively, the first and second photons optionally each irradiate the photonic structure at substantially the same angle as one another. Additionally, or alternatively, the first and second photons optionally each irradiate the photonic structure at an angle approximately normal to a major surface of the photonic structure. Additionally, or alternatively, the first and second photons optionally each irradiate the photonic structure at an angle approximately parallel to a major surface of the photonic structure.

Additionally, or alternatively, the second feature optionally is laterally displaced from the first feature.

Additionally, or alternatively, a third feature of the array of features optionally is disposed over the first pixel and spatially displaced from each of the first and second features. The device further optionally can include a third luminophore disposed within or over the third feature. The radiation source optionally can be configured to generate third photons having a third characteristic at a third time. Optionally, the third characteristic can be different than the first and second characteristics, and the third time can be different than the first and second times. Optionally, the first pixel selectively receives luminescence emitted by the third luminophore responsive to the third photons at the third time. Additionally, or alternatively, a fourth feature of the array of features optionally is disposed over the first pixel and spatially displaced from each of the first, second, and third features. The device optionally further includes a fourth luminophore disposed within or over the fourth feature. The radiation source optionally is configured to generate fourth photons having a fourth characteristic at a fourth time. Optionally, the fourth characteristic can be different than the first, second, and third characteristics, and the fourth time can be different than the first, second, and third times. The first pixel optionally selectively receives luminescence emitted by the fourth luminophore responsive to the fourth photons at the fourth time. Optionally, the first luminophore is coupled to a first nucleic acid, the second luminophore is coupled to a second nucleic acid, the third luminophore is coupled to a third nucleic acid, and the fourth luminophore is coupled to a fourth nucleic acid.

Additionally, or alternatively, a third feature of the array of features optionally is disposed over a second pixel of the array of imaging pixels, and a fourth feature of the array of features optionally is disposed over the second pixel and spatially displaced from the third feature. The device optionally further includes a third luminophore disposed within or over the third feature, and a fourth luminophore disposed within or over the fourth feature. Optionally, the second pixel selectively receives luminescence emitted by the third luminophore responsive to the first photons at the first time or responsive to the second photons at the second time. Optionally, the second pixel selectively receives luminescence emitted by the fourth luminophore responsive to the first photons at the first time or responsive to the second photons at the second time. Optionally, the first luminophore is coupled to a first nucleic acid, the second luminophore is coupled to a second nucleic acid, the third luminophore is coupled to a third nucleic acid, and the fourth luminophore is coupled to a fourth nucleic acid.

Additionally, or alternatively, the first and second features optionally each have a substantially circular cross-section. Additionally, or alternatively, the photonic structure optionally includes a hexagonal lattice, and optionally the imaging pixels are rectangular.

Additionally, or alternatively, the radiation source optionally is configured to flood illuminate the photonic structure with the first and second photons. Additionally, or alternatively, the radiation source optionally includes a laser. Additionally, or alternatively, optionally the first and second photons independently have wavelengths between about 300 nm and about 800 nm.

Additionally, or alternatively, the first luminophore optionally is coupled to a first nucleic acid, and the second luminophore optionally is coupled to a second nucleic acid. Additionally, or alternatively, the device optionally includes at least one microfluidic feature in contact with the array of features and configured to provide a flow of one or more analytes to the first and second features.

Additionally, or alternatively, the first luminophore optionally is coupled to a first polynucleotide to be sequenced, and the second luminophore optionally is coupled to a second polynucleotide to be sequenced. Optionally, the first polynucleotide is coupled to the first feature, and optionally the second polynucleotide is coupled to the second feature. Additionally, or alternatively, the device optionally further includes a first polymerase adding a first nucleic acid to a third polynucleotide that is complementary to and coupled to the first polynucleotide. The first nucleic acid optionally can be coupled to the first luminophore. The device optionally further includes a second polymerase adding a second nucleic acid to a fourth polynucleotide that is complementary to and coupled to the second polynucleotide. The second nucleic acid optionally can be coupled to the second luminophore. Optionally, the device further can include a channel flowing a first liquid including the first and second nucleic acids and the first and second polymerases into or over the first and second features.

Under another aspect, a method is provided for use in luminescent imaging. The method can include providing an array of imaging pixels, and providing a photonic structure disposed over the array of imaging pixels. The method further can include providing an array of features disposed over the photonic structure. A first feature of the array of features can be disposed over a first pixel of the array of imaging pixels, and a second feature of the array of features can be disposed over the first pixel and spatially displaced from the first feature. The method further can include providing a first luminophore disposed within or over the first feature, and providing a second luminophore disposed within or over the second feature. The method further can include generating by a radiation source first photons having a first characteristic at a first time, and generating by the radiation source second photons having a second characteristic at a second time. The second characteristic can be different than the first characteristic, and the second time can be different than the first time. The method further can include selectively receiving by the first pixel luminescence emitted by the first luminophore responsive to the first photons at the first time; and selectively receiving by the first pixel luminescence emitted by the second luminophore responsive to the second photons at the second time.

Optionally, the first photons having the first characteristic generate a first resonant pattern within the photonic structure at the first time, the first resonant pattern selectively exciting the first luminophore relative to the second luminophore. Optionally, the second photons having the second characteristic generate a second resonant pattern within the photonic structure at the second time, the second resonant pattern selectively exciting the second luminophore relative to the first luminophore.

Additionally, or alternatively, the array of imaging pixels, the photonic structure, and the array of features optionally are monolithically integrated with one another.

Additionally, or alternatively, the photonic structure optionally includes a photonic crystal, a photonic superlattice, a microcavity array, or an array of plasmonic nanoantennas.

Additionally, or alternatively, the array of features optionally includes a plurality of wells. The first feature optionally can include a first well within which the first luminophore is disposed, and the second feature optionally can include a second well within which the second luminophore is disposed. Alternatively, the array of features can include a plurality of posts. The first feature optionally can include a first post upon which the first luminophore is disposed, and the second feature optionally can include a second post upon which the second luminophore is disposed.

Additionally, or alternatively, the first and second characteristics optionally can be selected independently from the group consisting of wavelength, polarization, and angle. For example, the first characteristic optionally can include a first linear polarization, and the second characteristic optionally can include a second linear polarization that is different than the first linear polarization. Optionally, the first linear polarization can be substantially orthogonal to the second linear polarization, or can be rotated relative to the second linear polarization by between about 15 degrees and about 75 degrees. Additionally, or alternatively, the first characteristic optionally includes a first wavelength, and the second characteristic optionally includes a second wavelength that is different than the first wavelength.

Additionally, or alternatively, the radiation source optionally includes an optical component. The method optionally further includes controlling the optical component so as to impose the first characteristic on the first photons and so as to impose the second characteristic on the second photons. Optionally, the optical component includes a birefringent material rotating the first photons to a first linear polarization responsive to a first control signal by a controller, and rotating the second photons to a second linear polarization responsive to a second control signal by the controller.

Additionally, or alternatively, the first and second photons optionally each irradiate the photonic structure at substantially the same angle as one another. Additionally, or alternatively, the first and second photons optionally each irradiate the photonic structure at an angle approximately normal to a major surface of the photonic structure, or the first and second photons optionally each irradiate the photonic structure at an angle approximately parallel to a major surface of the photonic structure.

Additionally, or alternatively, the second feature optionally is laterally displaced from the first feature.

Additionally, or alternatively, a third feature of the array of features optionally is disposed over the first pixel and spatially displaced from each of the first and second features. Optionally, the method further includes providing a third luminophore disposed within or over the third feature, and generating third photons having a third characteristic at a third time. The third characteristic optionally can be different than the first and second characteristics, and the third time optionally can be different than the first and second times. The method optionally further can include selectively receiving by the first pixel luminescence emitted by the third luminophore responsive to the third photons at the third time. Optionally, a fourth feature of the array of features is disposed over the first pixel and spatially displaced from each of the first, second, and third features. The method optionally further includes providing a fourth luminophore disposed within or over the fourth feature, and generating fourth photons having a fourth characteristic at a fourth time. The fourth characteristic optionally can be different than the first, second, and third characteristics, the fourth time optionally can be different than the first, second, and third times. The method optionally further can include selectively receiving by the first pixel luminescence emitted by the fourth luminophore responsive to the fourth photons at the fourth time. Optionally, the first luminophore is coupled to a first nucleic acid, the second luminophore is coupled to a second nucleic acid, the third luminophore is coupled to a third nucleic acid, and the fourth luminophore is coupled to a fourth nucleic acid.

Additionally, or alternatively, a third feature of the array of features optionally can be disposed over a second pixel of the array of imaging pixels, and a fourth feature of the array of features is disposed over the second pixel and spatially displaced from the third feature. The method optionally further includes providing a third luminophore disposed within or over the third feature, and providing a fourth luminophore disposed within or over the fourth feature. The method optionally further includes selectively receiving by the second pixel luminescence emitted by the third luminophore responsive to the first photons at the first time or responsive to the second photons at the second time; and selectively receiving by the second pixel luminescence emitted by the fourth luminophore responsive to the first photons at the first time or responsive to the second photons at the second time. Optionally, the first luminophore is coupled to a first nucleic acid, the second luminophore is coupled to a second nucleic acid, the third luminophore is coupled to a third nucleic acid, and the fourth luminophore is coupled to a fourth nucleic acid.

Additionally, or alternatively, the first and second features optionally each have a substantially circular cross-section. Additionally, or alternatively, the photonic structure optionally includes a hexagonal lattice, and the imaging pixels optionally are rectangular.

Additionally, or alternatively, the method optionally includes flood illuminating the photonic structure with the first and second photons. Additionally, or alternatively, the method optionally includes generating the first and second photons with a laser. Additionally, or alternatively, optionally the first and second photons independently have wavelengths between about 300 nm and about 800 nm.

Additionally, or alternatively, the first luminophore optionally is coupled to a first nucleic acid, and the second luminophore optionally is coupled to a second nucleic acid. Additionally, or alternatively, the method optionally further includes providing at least one microfluidic feature in contact with the array of features and flowing, by the at least one microfluidic feature, one or more analytes to the first and second features.

Additionally, or alternatively, the first luminophore optionally is coupled to a first polynucleotide to be sequenced, and the second luminophore optionally is coupled to a second polynucleotide to be sequenced. Optionally, the first polynucleotide is coupled to the first feature, and the second polynucleotide optionally is coupled to the second feature. Additionally, or alternatively, the method optionally includes adding, by a first polymerase, a first nucleic acid to a third polynucleotide that is complementary to and coupled to the first polynucleotide. The first nucleic acid optionally can be coupled to the first luminophore. The method optionally further includes adding, by a second polymerase, a second nucleic acid to a fourth polynucleotide that is complementary to and coupled to the second polynucleotide. The second nucleic acid optionally can be coupled to the second luminophore. Optionally, the method further includes flowing, by a channel, a first liquid including the first and second nucleic acids and the first and second polymerases into or over the first and second features.

Under another aspect, a device is provided for use in luminescent imaging. The device can include an array of imaging pixels, and a photonic structure disposed over the array of imaging pixels. The device further can include an array of features disposed over the photonic structure. A first feature of the array of features can be disposed over a first pixel of the array of imaging pixels, and a second feature of the array of features can be disposed over the first pixel and spatially displaced from the first feature. The photonic structure can be tuned to selectively irradiate the first feature with light of a first polarization compared to light of a second polarization. The photonic structure can be tuned to selectively irradiate the second feature with light of a second polarization compared to light of the first polarization.

Optionally, the device further includes a radiation source configured to generate first photons having the first polarization at a first time, and configured to generate second photons having the second polarization at a second time.

Additionally, or alternatively, the device optionally further includes a first luminophore disposed within or over the first feature and a second luminophore disposed within or over the second feature.

Additionally, or alternatively, the device optionally further includes a first target analyte disposed within or over the first feature and a second target analyte disposed within or over the second feature. The first target analyte optionally can be different from the second target analyte. the first and second target analytes optionally include nucleic acids having different sequences.

BRIEF DESCRIPTION OF DRAWINGS

FIG. 5 schematically illustrates an exemplary photonic structure such as can be included in a device such as provided herein and illustrated in FIGS. 3A-3B.

FIGS. 6A-6D schematically illustrate exemplary simulated field strengths within a photonic structure such as illustrated in FIG. 5, for a radiation source that respectively generates photons having different characteristics than one another at different times.

FIG. 7A schematically illustrates a plan view of an exemplary photonic structurebased device such as provided herein and illustrated in FIGS. 3A-3B that includes first and second sites (e.g., clusters) per pixel.

FIG. 7B schematically illustrates exemplary simulated field strengths within an array of devices such as provided herein and illustrated in FIGS. 7A and 3A-3B for a radiation source generating photons having a first characteristic selectively exciting the first site at a first time.

FIG. 7C schematically illustrates exemplary simulated field strengths within an array of devices such as provided herein and illustrated in FIGS. 7A and 3A-3B for a radiation source generating photons having a second characteristic selectively exciting the second site at a second time.

FIG. 7D schematically illustrates exemplary cross-talk terms resulting from selective excitation of first and second sites such as provided herein and respectively illustrated in FIGS. 7B and 7C.

FIG. 8A schematically illustrates a plan view of an exemplary photonic structurebased device such as provided herein and illustrated in FIGS. 3A-3B that includes first, second, and third sites (e.g., clusters) per pixel.

FIG. 8B schematically illustrates exemplary simulated field strengths within an array of devices such as provided herein and illustrated in FIGS. 8A and 3A-3B for a radiation source generating photons having a first characteristic selectively exciting the first site at a first time.

FIG. 8C schematically illustrates exemplary simulated field strength within an array of devices such as provided herein and illustrated in FIGS. 8A and 3A-3B for a radiation source generating photons having a second characteristic selectively exciting the second site at a second time.

FIG. 8D schematically illustrates exemplary simulated field strength within an array of devices such as provided herein and illustrated in FIGS. 8A and 3A-3B for a radiation source generating photons having a third characteristic selectively exciting the third site at a third time.

FIG. 8E schematically illustrates exemplary cross-talk terms resulting from selective excitation of first, second, and third sites such as provided herein and respectively illustrated in FIGS. 8B-8D, according to some embodiments.

DETAILED DESCRIPTION

Figure 1A:
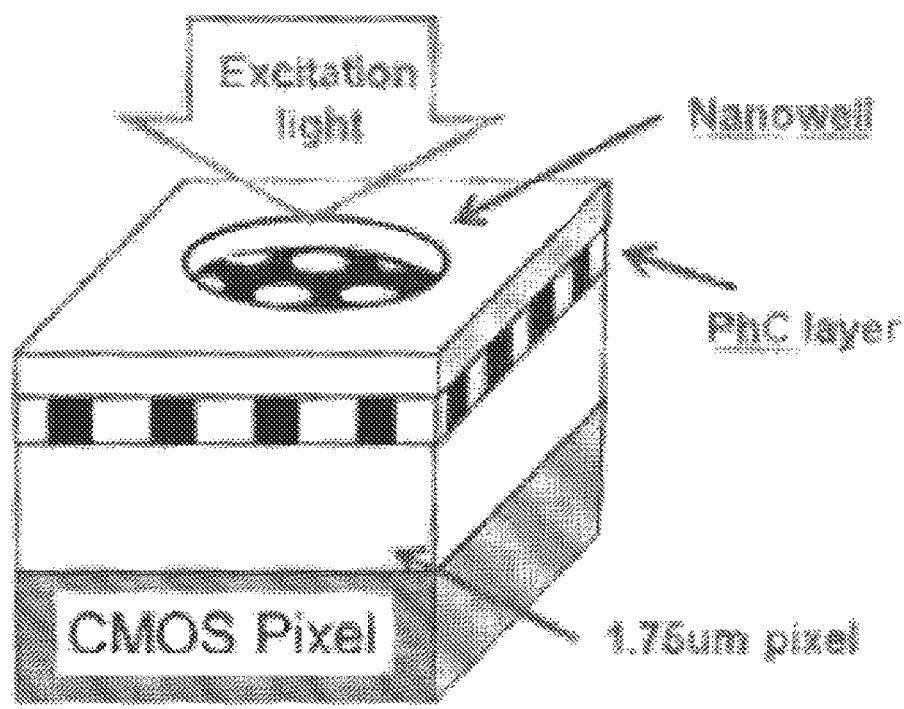
FIG. 1A schematically illustrates a perspective view of an exemplary prior art photonic structure-based device for use in luminescent imaging of a site within a pixel.

Embodiments of the present invention provide photonic structure-based devices and compositions for use in luminescent imaging of multiple sites within a pixel, and methods of using the same.

First, some exemplary terms will be defined, followed by further description of exemplary embodiments of the present photonic structure-based devices and compositions for use in luminescent imaging, and methods of using the same.

As used herein, the term "photonic structure" means a periodic structure, including one or more optically transparent materials, that selectively affects the propagation of radiation having a particular characteristic, e.g., at a wavelength, an angle, and at a polarization. For example, the photonic structure can selectively propagate radiation having such characteristic, e.g., at the wavelength, the angle, and the polarization, through the structure or at the same angle or a different angle out of the structure, and the field strength of such radiation can have a selected pattern within the photonic structure. Additionally, the structure can selectively inhibit propagation of radiation having a different characteristic, e.g., at a different wavelength, angle, and/or polarization, through the structure or at a different angle out of the structure, and/or the field strength of such radiation can have a different selected pattern within the photonic structure. The material(s) of the photonic structure can include features that are distributed in one or more dimensions, e.g., in one dimension, in two dimensions, or in three dimensions. The shape, size, and distribution of the features of the photonic structure, as well as the refractive index of the material(s), can be tuned so as select the particular radiation characteristic(s), e.g., wavelength(s), angle(s), or polarization(s), that can propagate through or at an angle out of the photonic structure, and/or so as to select the pattern of the field strength of such radiation within the photonic structure. Exemplary photonic structures include, but are not limited to, photonic crystals, photonic superlattices, microcavity arrays, and arrays of plasmonic nanoantennas.

As used herein, the terms "photonic crystal," "PhC," "photonic lattice," "photonic crystal lattice," and "PhC lattice" mean a photonic structure including one or more materials that include a periodic variation of refractive index on the order of the wavelength of light. For example, a photonic crystal can include a material that extends in three dimensions, e.g., has a length, a width, and a thickness. The material can have two major surfaces that each lie within a plane defined by the length and the width, and separated from one another by the thickness. The material can be patterned in two or more dimensions so as to define a photonic band structure within which radiation having particular characteristic(s), e.g., wavelength(s), angle(s), or polarization(s), can propagate through or at an angle out of the photonic crystal, and/or so as to select the pattern of the field strength of such radiation within the photonic crystal. The pattern can include, for example, a plurality of features such as wells or posts that are defined within the material, e.g., through one or both of the major surfaces of the material, the material being absent within or between the features, such as within the wells or between the posts. A space within or between the features can be filled with one or more additional materials that respectively can have different refractive indices than that of the material and than that of one another. The particular characteristic(s) of radiation, e.g., wavelength(s), angle(s), or polarization(s), that propagate or do not propagate through, or at an angle out of, the photonic crystal can be based on the refractive indices of the material and of any additional materials disposed within the features or between the features, as well as based on the characteristics of the features, such as the shape, size, and distribution of the features. The features can be all the same shape, size, and/or distribution as one another.

As used herein, the terms "photonic superlattice" and "PhC superlattice" mean a photonic structure that selectively affects the propagation of radiation having first and second characteristics, e.g., at first and second wavelength(s), angle(s), or polarization(s), compared to radiation having third characteristics, e.g., at a third wavelength, angle, or polarization. For example, the field strength of the radiation having the first characteristics can have a first pattern, and the field strength of the radiation having the second characteristics can have a second pattern that is different from the first pattern. The third wavelength can occur between the first and second wavelengths in the electromagnetic spectrum. For example, the photonic superlattice can selectively propagate radiation having the first and second characteristics, e.g., at the first and second wavelength(s), angle(s), or polarization(s), through the photonic superlattice or at an angle out of the photonic superlattice, and the patterns of the field strengths for the radiation having the first and second characteristics optionally can be different than one another. For example, the photonic superlattice can selectively inhibit propagation of radiation having the first and second characteristics, e.g., at the first and second wavelength(s), angle(s), or polarization(s), through the photonic superlattice or at an angle out of the photonic superlattice. For example, the photonic superlattice can selectively propagate radiation having third characteristics, e.g., at the third wavelength, angle, or polarization, through the photonic superlattice or at an angle out of the photonic superlattice. For example, the photonic superlattice can selectively inhibit propagation of radiation having third characteristics, e.g., at the third wavelength, angle, or polarization, through the structure or at an angle out of the structure. The material(s) can include features that are distributed in one or more dimensions, e.g., in one dimension, in two dimensions, or in three dimensions. The shape, size, and distribution of the features, as well as the refractive index of the material(s), can be tuned so as select the particular characteristics of radiation, e.g., wavelength(s), angle(s), or polarization(s), that can propagate through or at an angle out of the photonic superlattice, as well as the patterns of field strength of such characteristics, and so as to select the particular characteristics of radiation that do not propagate substantially through or at an angle out of the photonic superlattice.

Illustratively, a photonic superlattice can include a material that extends in three dimensions, e.g., has a length, a width, and a thickness. The material can have two major surfaces that each lie within a plane defined by the length and the width, and separated from one another by the thickness. The material can be patterned in two or more dimensions so as to define a photonic band structure that permits propagation of radiation having at least first and second characteristics, e.g., wavelength(s), angle(s), or polarization(s), within, or at an angle out of, the plane defined by the length and the width, and that inhibits propagation of at least radiation having third characteristics, e.g., a third wavelength, angle, or polarization, within, or at an angle out of, the material. The pattern can include, for example, a plurality of features such as wells or posts that are defined within the material, e.g., through one or both of the major surfaces of the material, the material being absent within or between the features, such as within the wells or between the posts. A space within or between the features can be filled with one or more additional materials that respectively can have different refractive indices than that of the material and than that of one another. The particular characteristics of radiation that propagate or do not propagate through, or at an angle out of, the photonic superlattice can be based on the refractive indices of the material and of any additional materials disposed within the features or between the features, as well as based on the characteristics of the features, such as the shape, size, and distribution of the features. Some of the features optionally can differ in at least one characteristic, e.g., shape, size, or distribution, from others of the features. For further details regarding exemplary photonic superlattices that can be used in the present devices, compositions, and methods, see U.S. Provisional Patent Application No. 62/312,704, filed Mar. 24, 2016 and entitled "Photonic Superlattice-Based Devices and Compositions for Use in Luminescent Imaging, and Methods of Using the Same," the entire contents of which are incorporated by reference herein.

As used herein, "microcavity array" means a periodic two-dimensional arrangement of photonic microresonators that support multiple (e.g., at least two, at least three, or at least four) resonances that can be excited independently of one another by changing a characteristic of an excitation source, such as the wavelength, polarization, or angle of the excitation source. For further details regarding exemplary microcavity arrays that can be used in the present devices, compositions, and methods, see Altug et al., "Polarization control and sensing with twodimensional coupled photonic crystal microcavity arrays," Opt. Lett. 30: 1422-1428 (2011), the entire contents of which are incorporated by reference herein.

As used herein, "array of plasmonic nanoantennas" means a periodic twodimensional arrangement of plasmonic nanostructures that support multiple (e.g., at least two, at least three, or at least four) resonances that can be excited independently of one another by changing a characteristic of an excitation source, such as the wavelength, polarization, or angle of the polarization source. For further details regarding exemplary plasmonic nanoantennas that can be used in the present devices, compositions, and methods, see Regmi et al., "Nanoscale volume confinement and fluorescence enhancement with double nanohole aperture," Scientific Reports 5: 15852-1-5 (2015), the entire contents of which are incorporated by reference herein.

One or more of the materials of the photonic structure can be or include a "dielectric material," meaning a fluidic, solid, or semi-solid material that is optically transparent and is an electrical insulator. Examples of fluidic dielectric materials include gases such as air, nitrogen, and argon, as well as liquids such as such as water, aqueous solvents, and organic solvents. Examples of solid dielectric materials include glasses (e.g., inorganic glasses such as silica, or modified or functionalized glasses) and polymers (such as acrylics, polystyrene, copolymers of styrene and other materials, polypropylene, polyethylene, polybutene, polyurethanes, TEFLON™, cyclic olefins, polyimides, or nylon). Examples of semi-solid dielectric materials include gels, such as hydrogels. Additionally, or alternatively, one or more materials of the photonic structure can be or include a solid semiconductor material that is optically transparent.

As used herein, the term "gel" is intended to mean a semi-solid or semi-rigid material that is permeable to liquids and gases. Typically, gel material can swell when liquid is taken up and can contract when liquid is removed by drying. Exemplary gels can include, but are not limited to, those having a colloidal structure, such as agarose or a hydrogel; polymer mesh structure, such as gelatin; or cross-linked polymer structure, such as polyacrylamide, SFA (see, for example, US 2011/0059865, the entire contents of which are incorporated by reference herein) or PAZAM (see, for example, US 2014/0079923, the entire contents of which are incorporated by reference herein). Particularly useful gel material will conform to the shape of a well or other concave feature where it resides.

As used herein, the term "well" means a discrete concave feature in a material having a surface opening (aperture) that is completely surrounded by interstitial region(s) of the surface. A well can have characteristics such as size (e.g., volume, diameter, and depth), cross-sectional shape (e.g., round, elliptical, triangular, square, polygonal, star shaped (having any suitable number of vertices), irregular, or having concentric wells separated by a dielectric material), and distribution (e.g., spatial locations of the wells within the dielectric material, e.g., regularly spaced or periodic locations, or irregularly spaced or aperiodic locations). The cross section of a well can be, but need not necessarily be, uniform along the length of the well.

As used herein, the term "post" means a discrete convex feature protruding from the surface of a material and that is completely surrounded by interstitial region(s) of the surface. A post can have characteristics such as size (e.g., volume, diameter, and depth), shape (e.g., round, elliptical, triangular, square, polygonal, star shaped (having any suitable number of vertices), irregular, or having concentric posts separated by a dielectric material), and distribution (e.g., spatial locations of the posts protruding from the surface of the dielectric material, e.g., regularly spaced or periodic locations, or irregularly spaced or aperiodic locations). The cross section of a post can be, but need not necessarily be, uniform along the length of the post.

As used herein, the term "surface" means a part or layer of a material that is in contact with another material.

As used herein, the term "interstitial region" is intended to mean an area in a material or on a surface that separates areas of the material or surface. For example, an interstitial region can separate one feature of a photonic structure from another feature of a photonic structure, or an interstitial region can separate one site of an array from another site of the array.

As used herein, the term "luminescent" means emitting cold body radiation, and the term "luminophore" means an item that is luminescent. The term "luminescent" is intended to be distinct from incandescence which is radiation emitted from a material as a result of heat. Generally luminescence results when an energy source displaces an electron of an atom out of its lowest energy ground state into a higher energy excited state; then the electron returns the energy in the form of radiation so it can fall back to its ground state. A particularly useful type of luminescent item is one that emits cold body radiation when energy is provided by excitation radiation. Such items can be referred to as "photoluminescent." Examples of photoluminescent items include "fluorescent" items that emit cold body radiation relatively quickly (e.g., less than a millisecond) after excitation radiation, and "phosphorescent" items that emit cold body radiation relatively slowly (e.g., greater than or equal to a millisecond) after excitation radiation. Photoluminescence can be perceived as emission of radiation by an item at a wavelength that is a result of irradiating the item at another wavelength. Another useful type of luminescent item is one that emits cold body radiation when energy is provided by a chemical or biological reaction. Such items can be referred to as "chemiluminescent."

Any of a variety of signals can be detected in a method set forth herein including, for example, an optical signal such as absorbance of radiation, luminescence emission, luminescence lifetime, luminescence polarization, or the like; Rayleigh and/or Mie scattering; or the like. Exemplary labels that can be detected in a method set forth herein include, without limitation, a fluorophore, luminophore, chromophore, nanoparticle (e.g., gold, silver, carbon nanotubes), or the like.

As used herein the term "feature" means a distinctive variation in the structure or composition of a material such as a solid support. Optionally, the variation is also repeated in the structure or composition of the material. A collection of the features can form an array or lattice in or on the material. Exemplary features include, but are not limited to wells, posts, ridges, channels, sites bearing analytes, layers of a multilayer material, areas in or on a material having a chemical composition that differ from the chemical composition of other areas in or on the material and the like. A feature can have characteristics such as size (e.g., volume, diameter, and depth), shape (e.g., round, elliptical, triangular, square, polygonal, star shaped (having any suitable number of vertices), irregular, or having concentric features separated by a dielectric material), and distribution (e.g., spatial locations of the features within the dielectric material, e.g., regularly spaced or periodic locations, or irregularly spaced or aperiodic locations). The cross section of a feature can be, but need not necessarily be, uniform along the length of the feature.

As used herein, the term "site" means a location in an array for a particular species of molecule or cell (or other analyte). A site can contain only a single molecule (or cell or other analyte) or it can contain a population of several molecules (or cells or analytes) of the same species. In some embodiments, sites are present on a material prior to attaching a particular analyte. In other embodiments the site is created by attachment of a molecule or cell (or other analyte) to the material. Sites of an array are typically discrete. The discrete sites can be contiguous or they can have spaces between each other. It will be understood that a site is a type of feature. A feature can function as a component of a lattice, array or both.

As used herein, the term "array" means a population of sites that can be differentiated from each other according to relative location.

As used herein, the term "pitch," when used in reference to features of a lattice (e.g. photonic structure) or array, is intended to refer to the center-to-center spacing for adjacent features of the lattice or array. A pattern of features can be characterized in terms of average pitch. The pattern can be ordered such that the coefficient of variation around the average pitch is small, or the pattern can be random in which case the coefficient of variation can be relatively large. In either case, the average pitch can be, for example, at least about on the order of a wavelength of light in one or more regions of the spectrum. For example, the pitch can correspond to wavelengths in one or more of the visible spectrum (about 380-700 nm), UV spectrum (less than about 380 nm to about 10 nm) and IR spectrum (greater than about 700 nm to about 1 mm). In a photonic structure, features can have different pitches than one another in different directions. For example, in a photonic superlattice, different types of features can have different pitches and patterns than one another. For example, the pitch for the features of one type (e.g. in a first lattice) can differ from the pitch for features of another type (e.g. in a second lattice).

As used herein, the term "random" can be used to refer to the spatial distribution, e.g., arrangement, of locations on a surface. For example, one or more features (e.g., wells or posts) of a photonic structure or a photonic superlattice can be randomly spaced such that nearest neighbor features, which can be of the same type or different type than one another, have variable spacing between each other. Alternatively, the spacing between features of the same type or a different type than one another can be ordered, for example, forming a regular pattern such as a rectilinear grid or a hexagonal grid.

As used herein, the term "nucleotide" or "nucleic acid" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), deoxyuridine triphosphate (dUTP), reversibly blocked adenosine triphosphate (rbATP), reversibly blocked thymidine triphosphate (rbTTP), reversibly blocked cytidine triphosphate (rbCTP), and reversibly blocked guanosine triphosphate (rbGTP). For further details on reversibly blocked nucleotide triphosphates (rbNTPs), see U.S. Patent Publication No. 2013/0079232, the entire contents of which are incorporated by reference herein.

The term "nucleotide" or "nucleic acid" also is intended to encompass any nucleotide analogue which is a type of nucleotide that includes a modified nucleobase, sugar and/or phosphate moiety. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "chemically coupled" is intended to mean an attachment between a first member and a second member. In some embodiments, such an attachment is normally irreversible under the conditions in which the attached members are used. In other embodiments, such an attachment is reversible but persists for at least the period of time in which it is used for one or more steps of an analytical or preparative technique set forth herein (e.g. an analytical step of detecting a subunit of a polymer). Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can be used to couple a first member to a second member. Other examples include duplexes between oligonucleotides, peptide-peptide interactions, and hapten-antibody interactions such as streptavidin-biotin, streptavidin-desthiobiotin, and digoxigenin-antidigoxigenin. In one embodiment, an attachment can be formed by hybridizing a first polynucleotide to a second polynucleotide that inhibits detachment of the first polynucleotide from the second polynucleotide. Alternatively, an attachment can be formed using physical or biological interactions, e.g., an interaction between a first protein and a second protein that inhibits detachment of the first protein from the second protein. As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

As used herein, the term "approximately" or "about" means within 10% of the stated value.

Provided herein are compositions and devices that include photonic structures, such as for single color or multicolor luminescence signal enhancement from analytes (e.g. DNA clusters) in one or more excitation and/or luminescence emission bands, optionally at normal incidence of excitation. For example, monolithic integration of photonic and microfluidic chips on top of CMOS imaging arrays can be used to reduce the size of, e.g., miniaturize, DNA sequencers. Throughput of CMOS-based sequencing devices can be limited by the size of imaging pixels. For example, relatively large pixel sizes can be useful for providing sufficient signal collection from individual DNA molecules or clusters of identical molecules. Although pixels can be made smaller so as to increase throughput, such size reduction can reduce full well capacity and can increase cross-talk between pixels, thereby reducing the signal-to-noise ratio (SNR) of the imaging, and the sequencing. Such an approach also can increase the cost of fabricating the imaging array, e.g., by increasing the amount of engineering of the imaging array as well as the integration of such imaging array with photonic and/or microfluidic components.

An alternative way of increasing throughout by providing more testing sites per device can involve introducing multiple luminescence sites (e.g., DNA clusters, microarray reaction chambers, or the like) per pixel. For example, in particular embodiments, the present compositions, devices, and methods can image multiple sites, each of which can include a respective analyte, using an imaging pixel by selectively exciting different sites at different times than one another using an excitation source, and obtaining a respective image at each such time. Illustratively, an array of imaging pixels can be provided, and multiple sites can be disposed over each such imaging pixel. Relative to a configuration in which only one site is disposed over a each given pixel, the present multi-site per pixel configuration can significantly increase the number of sites that can be imaged using a given pixel array. However, if all of the sites disposed over a given imaging pixel were to be excited simultaneously with one another, the pixel would receive luminescence from each such site simultaneously with one another, thus impeding the ability to distinguish between luminescence from one such site and luminescence from another such site based on an electrical signal that the pixel generates responsive to receiving such luminescence.

Optical techniques such as provided herein can be used so as selectively to excite only a single one of the multiple sites disposed over a given imaging pixel at a given time, so as to obtain an electrical signal from that pixel responsive to luminescence just from that site at that time, and subsequently to excite a second one of the multiple sites over that imaging pixel at a second time, so as to obtain a second electrical signal from that pixel responsive to luminescence from that second site. As such, the luminescence from the two sites can be distinguished from one another based on the electrical signals obtained from the imaging pixel at the two times. As such, the present compositions, devices, and methods can provide luminescent imaging of a greater number of sites than the number of pixels in an imaging array, e.g., an integer multiple n of the number of pixels, where n is greater than or equal to 2, or 3, or 4, or 5, or greater than 5.

As provided herein, the different sites disposed over an imaging pixel can be selectively excited by selectively directing excitation photons to respective ones of the sites at different times than one another. For example, a focused laser beam can be scanned over the different sites at different times than one another so as to selectively excite ones of the different sites at such times, the pixel generating electrical signals at such time responsive to the luminescence from the particular site being excited. As another example, the sites can be irradiated at a first time with any suitable number of laser beams that interfere with one another in such a manner as to generate a first optical intensity pattern that selectively excites one of the sites at the first time, and can be irradiated at a second time with any suitable number of laser beams that interfere with one another in such a manner as to generate a second optical intensity pattern that selectively excites another one of the sites at the second time. The pixel can generate respective electrical signals at the first and second times responsive to luminescence from the respective sites. As still another example, the sites can be disposed over or within a photonic structure that is disposed over the imaging pixel. The photonic structure can be configured so as selectively to excite one of the sites over the pixel responsive to irradiation with photons having a first characteristic at a first time, and selectively to excite another one of the sites over the pixel responsive to irradiation with photons having a second characteristic at a second time. The pixel can generate respective electrical signals at the first and second times responsive to luminescence from the respective sites.

The present photonic structure-based devices, compositions, and methods are compatible with previously known epifluorescence microscopy and microscope scanning systems (such as those in commercially available sequencing platforms such as produced by Illumina, Inc. (San Diego, Calif.)) that, in some circumstances, can use multiple fluorescent dyes excited at normal and imaged at normal incidence in various spectral windows. Such dyes can be coupled to nucleotides so as to facilitate sequencing polynucleotides such as DNA. However, it should be appreciated that the present photonic structure-based devices, compositions, and methods suitably can be used in any type of luminescent imaging or any other suitable application, and are not limited to use in sequencing polynucleotides such as DNA.

Patterning of dielectric substrates previously has been employed successfully to control the size and uniformity of polynucleotide clusters, and to increase the density of such clusters so as to improve throughput of sequencing. See for example, US Pat. App. Publ. No. 2014/0243224 A1, which is incorporated herein by reference. However, reduction in cluster size has resulted in a considerable reduction in the amount of collected multicolor fluorescence signal. For example, detection of weak multicolor fluorescence signals from large sampling areas can become increasingly difficult as the number of labeled nucleotides in DNA clusters is reduced (e.g., down to single-molecule levels or the resolution limits of the imaging system). Significant fluorescence signal enhancement therefore can be helpful to facilitate nucleotide identification and increase the throughput of next generation SBS systems.

For example, periodic patterning of materials, such as high-index dielectrics, in the proximity of fluorescently marked biomolecules can enhance fluorescence signal by creating one- or two-dimensional waveguides with a periodic variation of the refractive index in on the order of wavelength of light. Such waveguides, which can be referred to as photonic crystals (PhCs), photonic lattices, photonic crystal lattices, or PhC lattices, can support high-Q resonant modes that can boost fluorescent signals by resonantly enhancing fluorophore excitation, fluorescence collection, or both. For examples of use of single-color fluorescence signal enhancement using PhC lattices, see the following references, the entire contents of each of which are incorporated by reference herein: U.S. Pat. No. 7,768,640 to Cunningham et al.; Estrada et al., "Small volume excitation and enhancement of dye fluorescence on a 2D photonic crystal surface," Opt. Express 18: 3693-3699 (2010); Zhen et al., "Enabling enhanced emission and low-threshold lasing of organic molecules using special Fano resonances of macroscopic photonic crystals," PNAS 110: 13711-13716 (2013); Kaji et al., "Fabrication of two-dimensional $Ta_2O_5$ photonic crystal slabs with ultra-low background emission toward highly sensitive fluorescence spectroscopy," Opt. Express 19: 1422-1428 (2011); and Pokhriyal et al., "Photonic crystal enhanced fluorescence using a quartz substrate to reduce limits of detection," Opt. Express 18: 24793-24808 (2010).

PhC lattices also can be used in multicolor fluorescence signal enhancement. For example, dual-excitation fluorescence signal boost has been achieved with PhCs by resonant enhancement of excitation at different wavelengths that requires adjustment of the angle of incidence of excitation source to match the resonances supported by the PhC. For further details, see U.S. Pat. No. 8,344,333 to Lu et al., the entire contents of which are incorporated by reference herein. However, because the signal enhancement scheme described in Lu et al. operates in trans-fluorescence mode by tuning the illumination angles, such a scheme is not convenient for imaging or sequencing platforms that rely on multicolor epi-illumination at a fixed angle of incidence for all wavelengths of interest, e.g., a normal, or close to normal, angle of incidence.

FIG. 1A schematically illustrates a perspective view of an exemplary photonic structure-based device for use in luminescent imaging of a site within a pixel. The device illustrated in FIG. 1A includes an imaging pixel, such as a complementary metal oxide semiconductor (CMOS) based image sensor; a photonic structure such as a PhC layer disposed over the imaging pixel; and a nanowell defined within a third material disposed over the PhC layer. The PhC layer can include a first material (shown in black) having a refractive index of $n_1$, and regular patterns of uniformly shaped and sized wells that are defined within the first material and are filled with a second material (shown in white) having a refractive index of $n_2$, where $n_1$ and $n_2$ are different than each other. A site including one or more luminophores, e.g., one or more analytes respectively coupled to luminophores, e.g., one or more nucleotides respectively coupled to luminophores, can be disposed within the nanowell. The luminophore(s) can be disposed in the near field of the PhC layer and excited evanescently by the excitation wavelengths, e.g., photons having suitable characteristics (illustrated as large downward-pointing arrow in FIG. 1A). The imaging pixel can be suitably electronically coupled to a detection circuit (not specifically illustrated), which can be configured so as to receive and analyze an electrical signal generated by the imaging pixel responsive to luminescence generated by the luminophore(s). Although the imaging pixel is illustrated in FIG. 1A as having a dimension of 1.75 µm on each side, it should be appreciated that imaging pixels of any suitable dimensions can be used.

Figure 1B:
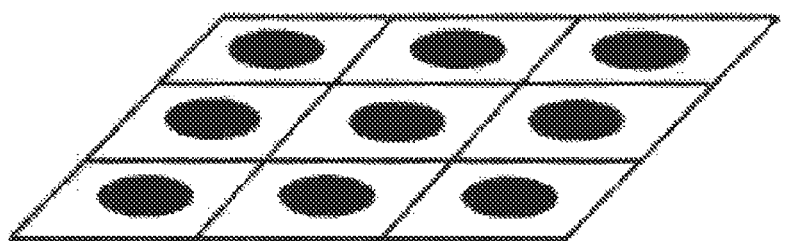
FIG. 1B schematically illustrates a perspective view of an exemplary prior art array of sites within an array of devices such as illustrated in FIG. 1A, wherein each site corresponds to a pixel.
Figure 1C:
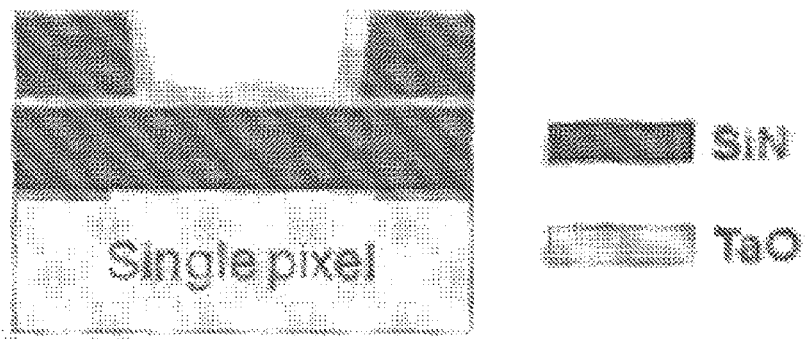
FIG. 1C schematically illustrates a cross-sectional view of an exemplary prior art device such as illustrated in FIG. 1A.

Optionally, an array of any suitable number of such devices can be provided. For example, FIG. 1B schematically illustrates a perspective view of an exemplary array of sites within an array of devices such as illustrated in FIG. 1A, wherein each site (represented as a black circle) corresponds to a pixel (represented as a rectangle). That is, the exemplary array illustrated in FIG. 1B includes one site for each pixel. Additionally, each such device can include any suitable number and type of materials. For example, FIG. 1C schematically illustrates a cross-sectional view of an exemplary device such as illustrated in FIG. 1A. In an exemplary embodiment of the device illustrated in FIGS. 1A-1C, a PhC layer can be disposed over any suitable imaging pixel such as known in the art. The PhC layer can include a first material, such as silicon nitride (SiN), that is patterned so as to define a photonic crystal. A second material, such as tantalum oxide (TaO), can be disposed over the PhC layer. The nanowell can be defined in a third material, such as SiN, and a fourth material such as TaO can be disposed over the nanowell. As illustrated in FIGS. 1A-1C, a single nanowell can be disposed over each imaging pixel. As such, each imaging pixel can receive luminescence from luminophore(s) disposed within the nanowell over that pixel, and generate a suitable electronic signal responsive to receipt of such luminescence.

Figure 2A:
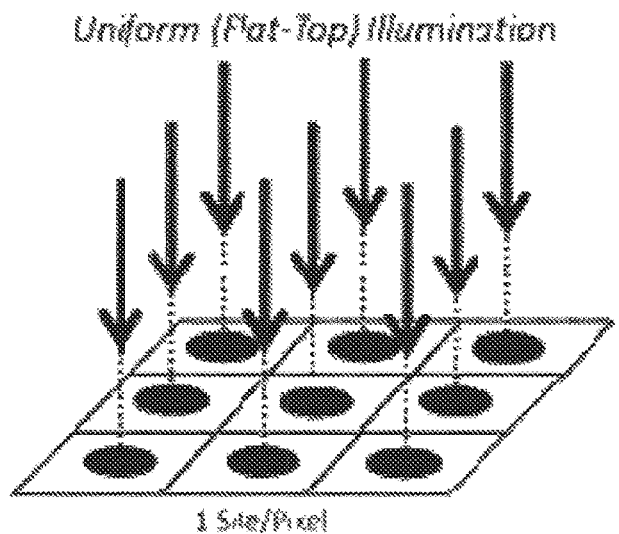
FIG. 2A schematically illustrates a perspective view of exemplary excitation of the prior art array of sites illustrated in FIG. 1B.
Figure 2B:
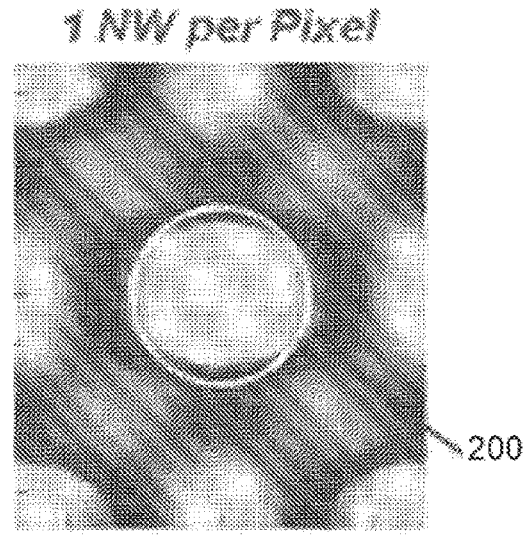
FIG. 2B schematically illustrates simulated exemplary prior art field strengths within an array of devices such as illustrated in FIGS. 1A and 1C responsive to excitation such as illustrated in FIG. 2A.

For example, FIG. 2A schematically illustrates a perspective view of exemplary excitation of the array of sites illustrated in FIG. 1B. Illustratively, the array of sites can be irradiated with uniform (flat-top) illumination from a single optical source, such as a laser. Such irradiation suitably can excite one or more resonant modes within the PhC beneath such sites (such as shown in FIGS. 1A and 1C). For example, FIG. 2B schematically illustrates simulated exemplary field strengths within an array of devices such as illustrated in FIGS. 1A and 1C responsive to excitation such as illustrated in FIG. 2A. The features of the PhC can be tuned so as to provide a relatively high field strength in a location disposed immediately beneath nanowell 200, thus selectively exciting luminophore(s) at the site disposed within that nanowell.

Figure 3A:
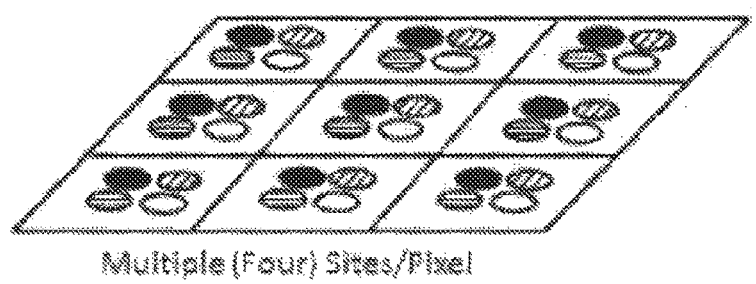
FIG. 3A schematically illustrates a perspective view of an exemplary array of sites such as provided herein, wherein multiple sites correspond to a pixel.
Figure 3B:
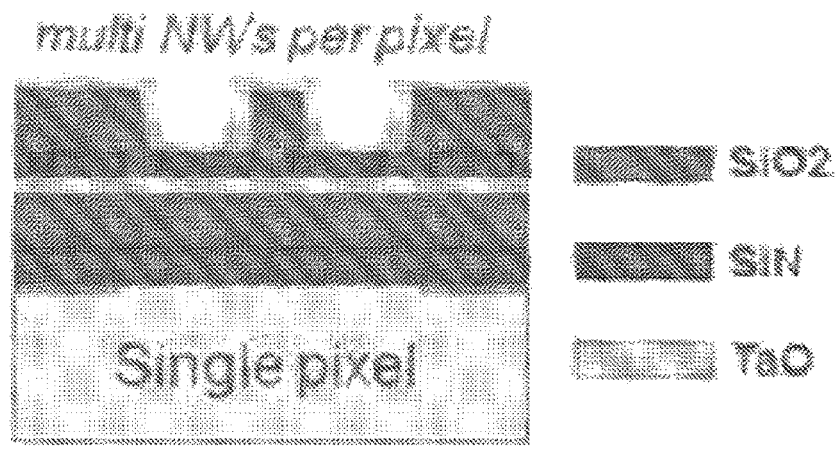
FIG. 3B schematically illustrates a cross-sectional view of a device such as provided herein, wherein multiple sites correspond to a pixel such as illustrated in FIG. 3A.

As provided herein, the number of sites can be increased as an integer multiple n>1 of the number of imaging pixels by selectively exciting different ones of such sites at different times than one another. For example, FIG. 3A schematically illustrates a perspective view of an exemplary array of sites such as provided herein, wherein multiple sites correspond to a pixel. In the non-limiting example illustrated in FIG. 3A, four sites (respectively illustrated as circles having different fills than one another) are provided per pixel (represented as rectangles), although it should be appreciated that any suitable number of sites can be provided per pixel, e.g., 2 or more sites per pixel, 3 or more sites per pixel, 4 or more sites per pixel, or 5 or more sites per pixel. Such sites can be provided using any suitable features. For example, FIG. 3B schematically illustrates a cross-sectional view of a device such as provided herein, wherein multiple sites correspond to a pixel such as illustrated in FIG. 3A. In an exemplary embodiment of the device illustrated in FIGS. 3A-3B, an optional photonic structure can be disposed over any suitable imaging pixel such as known in the art. The optional photonic crystal can include a first material, such as silicon nitride (SiN), that is disposed over the imaging pixel; a second material, such as silicon dioxide ($SiO_2$) that is disposed over the first material; and a photonic crystal including a pattern of a third material, such as SiN, and a fourth material, such as $SiO_2$. A fifth material, such as tantalum oxide (TaO), can be disposed over the PhC layer. A plurality of features, such as a plurality of nanowells, can be defined in a sixth material, such as $SiO_2$, and a seventh material such as TaO can be disposed over the plurality of nanowells. As illustrated in FIGS. 3A-3B, multiple features, e.g., multiple nanowells, can be disposed over each imaging pixel. As such, each imaging pixel can receive luminescence at different times from luminophore(s) disposed within or over each such feature, e.g., within each such nanowell, over that pixel, and generate a suitable electronic signal responsive to receipt of such luminescence at such different times. The imaging pixel, the optional photonic structure, and the features optionally can be monolithically integrated with one another.

It should be appreciated that the optional photonic structure illustrated in FIG. 3B is intended to be exemplary, and not limiting. For example, the photonic structure can include a photonic crystal, or a photonic superlattice, or a microcavity array, or an array of plasmonic nanoantennas.

Figure 4A:
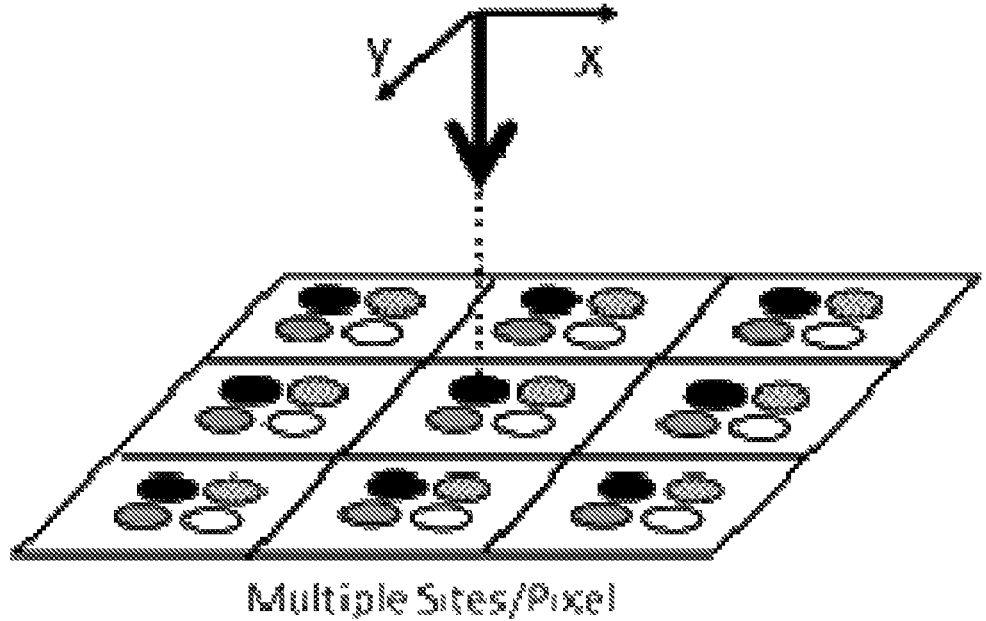
FIG. 4A schematically illustrates a perspective view of exemplary excitation of selected sites of the array of sites illustrated in FIG. 3A using scanning focused beam illumination such as provided herein.

Sites such as provided herein, e.g., with reference to FIGS. 3A-3B, selectively can be excited using any suitable technique. For example, a photonic structure optionally can be omitted, and the sites over a given pixel can be selectively excited by directing photons to such sites. Illustratively, a focused laser beam can be scanned over the different sites at different times than one another so as to selectively excite ones of the different sites at such times, the pixel generating electrical signals at such time responsive to the luminescence from the particular site being excited. For example, FIG. 4A schematically illustrates a perspective view of exemplary excitation of selected sites of the array of sites illustrated in FIG. 3A using scanning focused beam illumination such as provided herein. Illustratively, precise control of excitation beams can be achieved using high-precision free-space beam steering, or by sample manipulation, in a manner similar to that described in Hahn et al., "Laser scanning lithography for surface micropatterning on hydrogels," Adv. Mater. 17: 2939-2942 (2005) or that described in Brakenhoff et al., "Confocal light scanning microscopy with high-aperture immersion lenses," J. Microsc. 117: 219-232 (1997), the entire contents of both of which are incorporated by reference herein.

Figure 4B:
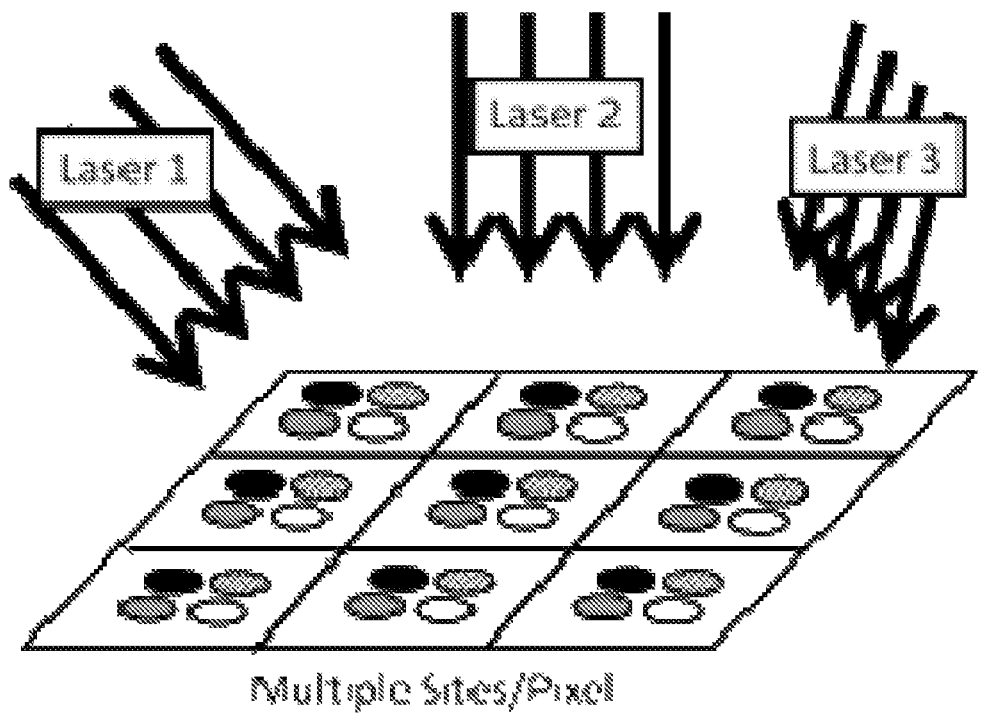
FIG. 4B schematically illustrates a perspective view of exemplary excitation of selected sites of the array of sites illustrated in FIG. 3A using multi-laser interference illumination such as provided herein.

As another example, the sites can be irradiated at a first time with any suitable number of laser beams that interfere with one another in such a manner as to generate a first optical intensity pattern that selectively excites one of the sites at the first time, and can be irradiated at a second time with any suitable number of laser beams that interfere with one another in such a manner as to generate a second optical intensity pattern that selectively excites another one of the sites at the second time. The pixel can generate respective electrical signals at the first and second times responsive to luminescence from the respective sites. For example, FIG. 4B schematically illustrates a perspective view of exemplary excitation of selected sites of the array of sites illustrated in FIG. 3A using multi-laser interference illumination such as provided herein. The sites selectively can be irradiated using multi-laser interference illumination similar to that described in van Wolferen et al., "Laser interference lithography," in Lithography: Principles, Processes and Materials, pages 133-148, Theodore Hennessy, Ed., Nova Science Publishers, Inc. (2011), or in He et al., "Polarization control in flexible interference lithography for nano-patterning of different photonic structures with optimized contrast," Optics Express 11518-11525 (May 4, 2015), the entire contents of each of which are incorporated by reference herein.

As still another example, the sites can be disposed over or within a photonic structure that is disposed over the imaging pixel. The photonic structure can be configured so as selectively to excite one of the sites over the pixel responsive to irradiation with photons having a first characteristic at a first time, and selectively to excite another one of the sites over the pixel responsive to irradiation with photons having a second characteristic at a second time. The pixel can generate respective electrical signals at the first and second times responsive to luminescence from the respective sites. For example, FIG. 5 schematically illustrates an exemplary photonic structure such as can be included in a device such as provided herein and illustrated in FIGS. 3A3B. In the particular embodiment illustrated in FIG. 5, the photonic structure can include a photonic crystal (PhC), but it should be appreciated that the photonic structure can include a photonic superlattice, or a microcavity array, or an array of plasmonic nanoantennas. The exemplary PhC illustrated in FIG. 5 includes a hexagonal array of features defined within a material, where the spacing $\Lambda_{PhC}$ between the features is on the order of the wavelength of excitation light $\lambda_{excitation}$.

The photonic structure, e.g., PhC, can be tuned (e.g., the features of the PhC can be selected) such that photons having different characteristics than one another can selectively excite different resonances within the PhC. Photonic structure design parameters can be computationally adjusted so as to tune resonances to respective desired locations and/or excitation or emission peaks of luminophores, for example using one or more of Finite-Difference Time-Domain (FDTD), Rigorous Coupled-Wave Analysis (RCWA), and Plane-Wave Expansion (PWE). Design optimization can employ multi-parameter sweeps or selfoptimization algorithms to maximize luminescence signal, e.g., fluorescence signal, in desired physical regions and/or spectral regions. For example, the refractive indices of material(s) that a photonic structure is to include, the spatial locations at which high field intensity is desired, and the wavelengths for which it is desired that the photonic structure selectively support resonances, can be computationally defined, and any suitable combination of FDTD, RCWA, PWE, or any other suitable optimization program(s) can be used so as to adjust other parameters of the structure, such as the size, shape, and distribution of features within the structure, so as to explore the design parameter space of the structure and to identify combinations of parameters that align the spectral and spatial features of the structure with the desired luminophore location and/or excitation or emission wavelengths.

For example, FIGS. 6A-6D schematically illustrate exemplary simulated field strengths within a photonic crystal such as illustrated in FIG. 5, for a radiation source that respectively generates photons having different characteristics than one another at different times. The simulated photonic crystal included a hexagonal array of air holes in a $Ta_2O_5$ film positioned on top of an $SiO_2$ substrate. More specifically, FIG. 6A illustrates simulated field strengths within the exemplary photonic crystal of FIG. 5 for photons having a first polarization at a first time, e.g., X-polarization; FIG. 6B illustrates simulated field strengths within that photonic crystal for photons having a second polarization at a second time, e.g., Y-polarization; FIG. 6C illustrates simulated field strengths within that photonic crystal for photons having a third polarization at a third time, e.g., RX-polarization; and FIG. 6D illustrates simulated field strengths within that photonic crystal for photons having a fourth polarization at a fourth time, e.g., RY-polarization. Based on FIGS. 6A-6D, it can be understood that by varying the polarization of the photons, different patterns of field strengths within the photonic crystal can be excited. It should be appreciated that by different patterns of field strengths varying other characteristics of the photons, such as the wavelength or angle of the photons, different patterns of field strengths within the photonic crystal similarly can be excited. Similar differences in patterns of field strengths for any suitable types of photonic structures, such as photonic crystals, photonic superlattices, microcavity arrays, or arrays of plasmonic nanoantennas, similarly can be obtained by suitably tuning the features of the photonic structures and suitably varying the characteristics of photons irradiating that structure at different times than one another.

In some embodiments, the present devices, compositions, and methods can provide multiple luminophore-including sites that respectively spatially overlap with different patterns of field strengths that are excited at different times than one another. For example, FIG. 7A schematically illustrates a plan view of an exemplary photonic structure-based device such as provided herein and illustrated in FIGS. 3A-3B that includes first and second sites (e.g., clusters) per pixel. The device can include an array of imaging pixels, a photonic structure disposed over the array of imaging pixels; and an array of features disposed over the photonic structure. The photonic structure can, for example, include a photonic crystal, a photonic superlattice, a microcavity array, or an array of plasmonic nanoantennas. The array of imaging pixels, the photonic structure, and the array of features optionally can be monolithically integrated with one another. In one nonlimiting example, the photonic structure can include a hexagonal lattice, and the imaging pixels can be rectangular.

A first feature of the array of features can be disposed over a first pixel of the array of imaging pixels, and a second feature of the array of features can be disposed over the first pixel and spatially displaced from the first feature. For example, in the non-limiting example illustrated in FIG. 7A, a first feature (referred to as "Cluster 1") and a second feature (referred to as "Cluster 2") both are disposed over the same pixel as one another. The second feature can be laterally displaced from the first feature in a manner such as illustrated in FIG. 7A. In one example, the first and second features respectively are positioned at the bottom-right and top-left corners of the metal light-shield aperture above the pixel, respectively. A first luminophore can be disposed within or over the first feature, and a second luminophore can be disposed within or over the second feature. For example, in some embodiments, the array of features can include a plurality of wells; the first feature can include a first well within which the first luminophore is disposed, and the second feature can include a second well within which the second luminophore is disposed, e.g., in a manner similar to that illustrated in FIG. 3B. In other embodiments, the array of features can include a plurality of posts; the first feature can include a first post upon which the first luminophore is disposed, and the second feature can include a second post upon which the second luminophore is disposed. Illustratively, the first and second features (e.g., wells or posts) each can have a substantially circular cross-section.

The device further can include a radiation source configured to generate first photons having a first characteristic at a first time, and configured to generate second photons having a second characteristic at a second time, the second characteristic being different than the first characteristic, the second time being different than the first time. In contrast to embodiments such as described herein with reference to FIGS. 4A-4B, the radiation source need not necessarily be configured so as to selectively direct radiation to different sites at different times. Instead, in some embodiments, the radiation source can be configured so as respectively to flood illuminate the photonic structure with the first and second photons at the first and second times, and the features of the photonic structure selectively can direct radiation to the different sites. Additionally, or alternatively, the radiation source can include a laser. Optionally, the first and second photons emitted by the radiation source can be in the optical range of the spectrum, e.g., the first and second photons independently have wavelengths between about 300 nm and about 800 nm.

In some embodiments, the photonic structure can be tuned so as to selectively irradiate the first feature with light of a first polarization compared to light of a second polarization, and can be tuned to selectively irradiate the second feature with light of a second polarization compared to light of the first polarization. For example, the device can include a first luminophore disposed within or over the first feature and a second luminophore disposed within or over the second feature. Illustratively, the device can include a first target analyte disposed within or over the first feature and a second target analyte disposed within or over the second feature, wherein the first target analyte is different from the second target analyte. Optionally, the first and second target analytes can include nucleic acids having different sequences.

In some embodiments, the first pixel can selectively receive luminescence emitted by the first luminophore responsive to the first photons at the first time, and can selectively receive luminescence emitted by the second luminophore responsive to the second photons at the second time. For example, the first photons having the first characteristic can generate a first resonant pattern within the photonic structure at the first time, the first resonant pattern selectively exciting the first luminophore relative to the second luminophore. Illustratively, FIG. 7B schematically illustrates exemplary simulated field strengths within an array of devices such as provided herein and illustrated in FIGS. 7A and 3A-3B for a radiation source generating photons having a first characteristic selectively exciting the first site at a first time. It can be seen that the photons having the first characteristic generate a spatial pattern of field strengths that is significantly more intense at the first feature than at the second feature, and thus can selectively excite the first luminophore relative to the second luminophore at the first time. As such, the imaging pixel can generate an electrical signal at the first time that substantially corresponds to selective excitation of the first luminophore disposed within or over the first feature.

Additionally, the second photons having the second characteristic can generate a second resonant pattern within the photonic structure at the second time, the second resonant pattern selectively exciting the second luminophore relative to the first luminophore. Illustratively, FIG. 7C schematically illustrates exemplary simulated field strengths within an array of devices such as provided herein and illustrated in FIGS. 7A and 3A-3B for a radiation source generating photons having a second characteristic selectively exciting the second site at a second time. It can be seen that the photons having the second characteristic generate a spatial pattern of field strengths that is significantly more intense at the second feature than at the first feature, and thus can selectively excite the second luminophore relative to the first luminophore at the second time. As such, the imaging pixel can generate an electrical signal at the second time that substantially corresponds to selective excitation of the second luminophore disposed within or over the second feature. Accordingly, two or more luminophores that are within the detection zone of a particular pixel can be distinguished from each other using spatial patterns of excitation light applied to the luminophores at different times. This combination of spatial and temporal separation of excitation events can allow the pixel to distinguish the two or more luminophores within its detection zone.

Note that although the first luminophore can be excited selectively relative to the second luminophore at the first time such as illustrated in FIG. 7B, the second luminophore nonetheless can be excited at the first time, to a smaller extent than is the first luminophore. Similarly, although the second luminophore can be excited selectively relative to the first luminophore at the second time such as illustrated in FIG. 7C, the first luminophore nonetheless can be excited at the second time, to a smaller extent than is the second luminophore. Such excitation of the second luminophore at the first time and of the first luminophore at the second time can be referred to as "cross-talk." FIG. 7D schematically illustrates exemplary cross-talk terms resulting from selective excitation of first and second sites such as provided herein and respectively illustrated in FIGS. 7B and 7C. The photonic structure and/or the respective characteristics of the first and second photons can be tuned so as to reduce cross-talk to a level at which respective luminescence from the first and second luminophores suitably can be distinguished from one another.

In embodiments such as illustrated in FIGS. 7B and 7C, the first and second characteristics of the first and second photons can be selected independently from the group consisting of wavelength, polarization, and angle. Illustratively, the first characteristic can include a first linear polarization, and the second characteristic can include a second linear polarization that is different than the first linear polarization. As one example, the first linear polarization can be substantially orthogonal to the second linear polarization. Illustratively, the pattern of field strengths illustrated in FIG. 7B, which selectively excites the first luminophore within or over the first feature, is generated using photons having a first linear polarization, such as X-polarization; and the pattern of field strengths illustrated in FIG. 7C, which selectively excites the second luminophore within or over the second feature, is generated using photons having a second linear polarization that is substantially orthogonal to the first linear polarization, such as Y-polarization. However, it should be appreciated that the photons at the first and second times can have any suitable polarizations. For example, the first linear polarization can be rotated relative to the second linear polarization by between about 15 degrees and about 75 degrees, e.g., so as to generate other patterns of field strengths such as described herein with reference to FIGS. 6A-6D. As another example, the polarization axes can be rotated clockwise by 30 degrees and rotated X- and Y-polarized beams (RX- and RY-polarized beams) can be used. Additionally, it should be appreciated that the photons at the first and second times respectively can have any other suitable characteristics. For example, the first characteristic of the photons at the first time can include a first wavelength, and the second characteristic of the photons at the second time can include a second wavelength that is different than the first wavelength.

The characteristics of the first and second photons generated at the first and second times can be controlled in any suitable manner. For example, in some embodiments, the radiation source of the device can include an optical component and a controller coupled to the optical component. The controller suitably can be configured to control the optical component so as to impose the first characteristic on the first photons and configured to impose the second characteristic on the second photons. For example, in embodiments where the respective photon characteristics include polarization, the optical component can include a birefringent material configured to rotate the first photons to a first linear polarization responsive to a first control signal by the controller, and configured to rotate the second photons to a second linear polarization responsive to a second control signal by the controller. In embodiments where the respective photon characteristics include wavelength, the optical component can include an electronically adjustable filter disposed in the path of the photons that can be adjusted so as to control the wavelength of photons arriving at the photonic structure responsive to control signals by the controller, or can include a portion of the radiation source that can be adjusted so as to control the wavelength of photons being generated at a given time by the radiation source responsive to control signals by the controller. In embodiments where the respective photon characteristics include angle, the optical component can include a reflective or transmissive optic, such as a lens and/or mirror, that can be adjusted so as to control the angle of photons arriving at the photonic structure responsive to control signals by the controller. It should be appreciated that more than one photon characteristic can be varied at a time. For example, any suitable combination of two or more of the wavelength, angle, and polarization of the photons can be adjusted so as selectively to excite a given luminophore disposed over a pixel relative to another luminophore disposed over that pixel.

In some embodiments, the first and second photons can irradiate the photonic structure at any suitable angle. For example, the first and second photons each can irradiate the photonic structure at substantially the same angle as one another, illustratively at an angle approximately normal to a major surface of the photonic structure, or at an angle approximately parallel to a major surface of the photonic structure.

In embodiments such as illustrated in FIGS. 7A-7D, it should be appreciated that other features of the array of features can be disposed over other pixels. For example, a third feature of the array of features can be disposed over a second pixel of the array of imaging pixels, and a fourth feature of the array of features can be disposed over the second pixel and spatially displaced from the third feature. The device further can include a third luminophore disposed within or over the third feature, and a fourth luminophore disposed within or over the fourth feature. The second pixel can selectively receive luminescence emitted by the third luminophore responsive to the first photons at the first time or responsive to the second photons at the second time, for example, if the third luminophore can be excited by the first photons or by the second photons. The second pixel selectively can receive luminescence emitted by the fourth luminophore responsive to the first photons at the first time or responsive to the second photons at the second time, for example, if the fourth luminophore can be excited by the first photons or by the second photons.

It also should be appreciated that any suitable number of sites can be provided per pixel. Illustratively, a device such as illustrated in FIGS. 3A-3B and 7A-7D optionally further can include a third feature of the array of features that is disposed over the first pixel and spatially displaced from each of the first and second features. The device can include a third luminophore disposed within or over the third feature. The radiation source can be configured to generate third photons having a third characteristic at a third time, the third characteristic being different than the first and second characteristics, the third time being different than the first and second times. The first pixel can selectively receive luminescence emitted by the third luminophore responsive to the third photons at the third time. For example, FIG. 8A schematically illustrates a plan view of an exemplary photonic structure-based device such as provided herein and illustrated in FIGS. 3A-3B that includes first, second, and third sites (e.g., clusters) per pixel (represented as circles). In a manner similar to that described above with reference to FIGS. 6A-6D and 7A-7C, the photonic structure respectively can be irradiated with photons having first, second, and third characteristics at first, second, and third times, so as respectively to excite the first, second, and third luminophores at the first, second, and third sites at such times.

For example, FIG. 8B schematically illustrates exemplary simulated field strengths within an array of devices such as provided herein and illustrated in FIGS. 8A and 3A-3B for a radiation source generating photons having a first characteristic selectively exciting the first site at a first time. FIG. 8C schematically illustrates exemplary simulated field strength within such an array of devices for a radiation source generating photons having a second characteristic selectively exciting the second site at a second time. FIG. 8D schematically illustrates exemplary simulated field strength within such an array of devices a radiation source generating photons having a third characteristic selectively exciting the third site at a third time. As one example, the first characteristic can include a first linear polarization, e.g., Y-polarization, the second characteristic can include a second linear polarization, e.g., RY-polarization, and the third characteristic can include a third linear polarization, e.g., RX-polarization. Note that one or more of such polarizations can be, but need not necessarily be, orthogonal to one another. For example, the RX- and RY-polarizations are orthogonal to one another, and each are at an angle between about 15 degrees and about 75 degrees to the Y-polarization, e.g., 45 degrees. For example, the first linear polarization can be rotated relative to the second linear polarization by between about 15 degrees and about 75 degrees, e.g., so as to generate other patterns of field strengths such as described herein with reference to FIGS. 6A-6D. As another example, the polarization axes can be rotated clockwise by 30 degrees and rotated X- and Y-polarized beams (RX- and RY-polarized beams) can be used. Additionally, note that in a manner similar to that described above with reference to FIG. 7D, selectively exciting the first site at the first time also may excite the second and/or third sites to a lesser degree, selectively exciting the second site at the second time also may excite the first and/or third sites, and/or selectively exciting the third site at the third time also may excite the first and/or second sites. FIG. 8E schematically illustrates exemplary cross-talk terms resulting from selective excitation of first, second, and third sites such as provided herein and respectively illustrated in FIGS. 8B-8D, according to some embodiments. The photonic structure and/or the respective characteristics of the first and second photons can be tuned so as to reduce cross-talk to a level at which respective luminescence from the first and second luminophores suitably can be distinguished from one another.

Figure 9A:
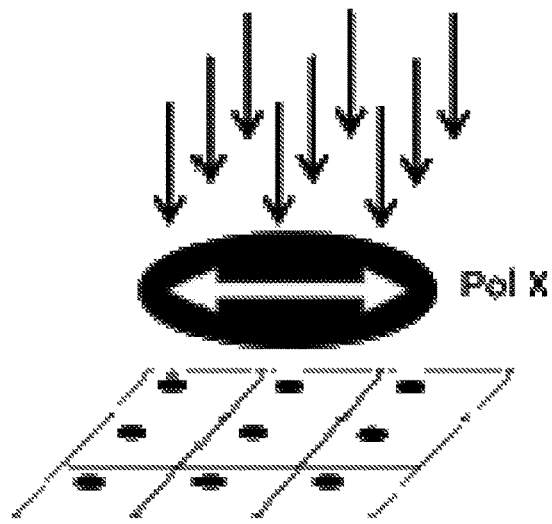
FIGS. 9A-9D respectively schematically illustrate perspective views of exemplary selective excitation of first, second, third, and fourth sites within an array of devices such as provided herein and illustrated in FIGS. 3A-3B using a radiation source generating photons having different characteristics at different times.
Figure 9B:
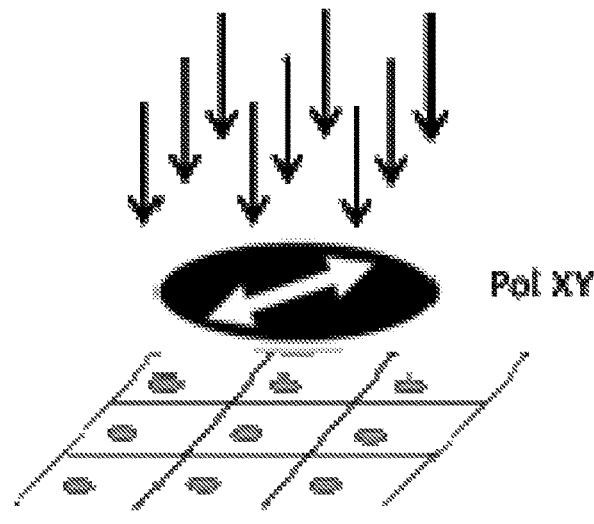
Figure 9C:
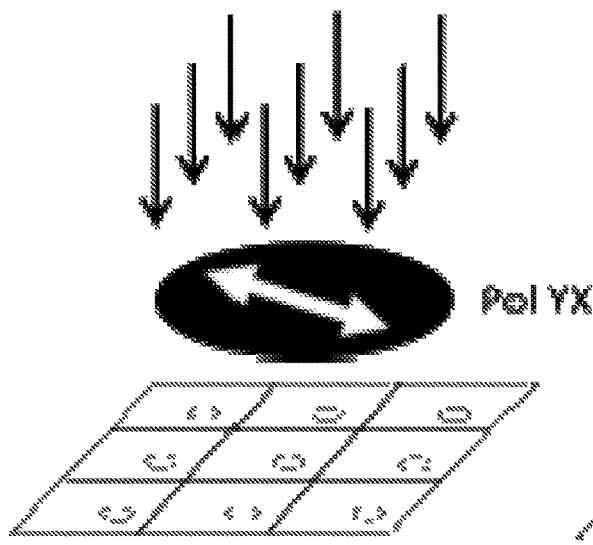
Figure 9D:
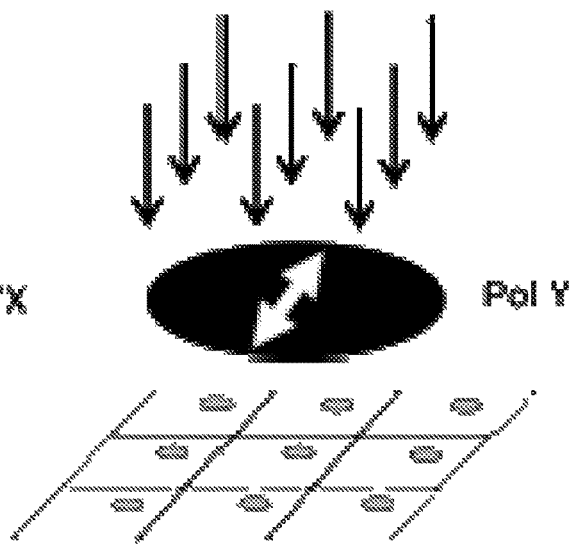

The present devices suitably further can include an even greater number of sites disposed over each pixel. For example, the device such as described above with reference to FIGS. 3A-3B and 8A-8E optionally further can include a fourth feature of the array of features that is disposed over the first pixel and spatially displaced from each of the first, second, and third features. The device further can include a fourth luminophore disposed within or over the fourth feature. The radiation source can be configured to generate fourth photons having a fourth characteristic at a fourth time, the fourth characteristic being different than the first, second, and third characteristics, the fourth time being different than the first, second, and third times. The first pixel can selectively receive luminescence emitted by the fourth luminophore responsive to the fourth photons at the fourth time. Illustratively, FIGS. 9A-9D respectively schematically illustrate perspective views of exemplary selective excitation of first, second, third, and fourth sites within an array of devices such as provided herein and illustrated in FIGS. 3A-3B using a radiation source generating photons having different characteristics at different times. For example, in a manner such as illustrated in FIG. 9A, at a first time the photonic structure can be irradiated with photons having a first characteristic (e.g., a first polarization, such as Xpolarization) so as selectively to excite a first site disposed over each pixel. Subsequently, in a manner such as illustrated in FIG. 9B, at a second time the photonic structure can be irradiated with photons having a second characteristic (e.g., a second polarization, such as XYpolarization) so as selectively to excite a second site disposed over each pixel. Subsequently, in a manner such as illustrated in FIG. 9C, at a third time the photonic structure can be irradiated with photons having a third characteristic (e.g., a third polarization, such as YX-polarization) so as selectively to excite a third site disposed over each pixel. Subsequently, in a manner such as illustrated in FIG. 9D, at a fourth time the photonic structure can be irradiated with photons having a fourth characteristic (e.g., a fourth polarization, such as Y-polarization). The pixels respectively can generate electrical signals at the first, second, third, and fourth times, based upon which the first, second, third, and fourth sites disposed over such pixels can be distinguished from one another.

The present compositions, devices, and methods suitably can be used so as to generate luminescent images in SBS sequencing fluorescence signal enhancement at normal incidence illumination. For example, the device further can include at least one microfluidic feature in contact with the array of features and configured to provide a flow of one or more analytes to the first and second features. Additionally, or alternatively, the present compositions, devices, and methods can enhance excitation efficiency of any suitable number of luminophores using any suitable number of excitation wavelengths, e.g., can enhance excitation efficiency of four distinct excitation sources at four resonant wavelengths ($\square_1$, $\square_2$, $\square_3$, and $\square_4$) in a 4-channel SBS chemistry scheme, or can enhance excitation efficiency at two excitation wavelengths ($\square_1$ and $\square_2$) in a 2-channel SBS chemistry scheme, or can enhance excitation efficiency at one excitation wavelength ($\square_1$) in a 1-channel SBS chemistry scheme. Exemplary 4-channel, 3channel, 2-channel or 1-channel SBS schemes are described, for example, in US Pat. App. Pub. No. 2013/0079232 A1 (incorporated herein by reference) and can be modified for use with the apparatus and methods set forth herein. For example, referring again to embodiments such as described with reference to FIGS. 7A-7D in which first and second luminophores are disposed over a first pixel, the first luminophore can be coupled to a first nucleic acid, and the second luminophore can be coupled to a second nucleic acid. As another example, referring to the optional embodiment described with reference to FIGS. 7A-7D in which first and second luminophores are disposed over a first pixel and third and fourth luminophores are disposed over a second pixel, the first luminophore can be coupled to a first nucleic acid, the second luminophore can be coupled to a second nucleic acid, the third luminophore is coupled to a third nucleic acid, and the fourth luminophore can be coupled to a fourth nucleic acid. As still another example, referring again to the illustrative embodiments described with reference to FIGS. 9A9D, the first luminophore can be coupled to a first nucleic acid, the second luminophore can be coupled to a second nucleic acid, the third luminophore can be coupled to a third nucleic acid, and the fourth luminophore can be coupled to a fourth nucleic acid. For example, in compositions for use in sequencing DNA using luminescent imaging, the first luminophore can be coupled to A, the second luminophore can be coupled to G, the third luminophore can be coupled to C, and the fourth luminophore can be coupled to T. As another example, in compositions for use in sequencing RNA using luminescent imaging, the first luminophore can be coupled to A, the second luminophore can be coupled to G, the third luminophore can be coupled to C, and the fourth luminophore can be coupled to U.

In devices such as provided herein, e.g., such as described with reference to any of FIG. 3A-3B, 7A-7D, 8A-8E, or 9A-9D, the first luminophore can be coupled to a first polynucleotide to be sequenced, and the second luminophore can be coupled to a second polynucleotide to be sequenced. For example, the first polynucleotide can be coupled to the first feature, and the second polynucleotide can be coupled to the second feature. The device can further include a first polymerase adding a first nucleic acid to a third polynucleotide that is complementary to and coupled to the first polynucleotide, the first nucleic acid being coupled to the first luminophore. The device further can include a second polymerase adding a second nucleic acid to a fourth polynucleotide that is complementary to and coupled to the second polynucleotide, the second nucleic acid being coupled to the second luminophore. The device further can include a channel flowing a first liquid including the first and second nucleic acids and the first and second polymerases into or over the first and second features. For example, the first and second polynucleotides can be coupled to the first and second features that are disposed over a first pixel, and that are to be sequenced using a suitable SBS scheme. The first and second luminophores respectively can be coupled to first and second nucleic acids that respectively are being incorporated into the first and second polynucleotides, e.g., using the first and second polymerases. Following an SBS step of incorporating the first and second nucleic acids into the first and second polynucleotides, the first and second luminophores selectively can be luminescently imaged at different times than one another in a manner such as provided herein, so as to obtain respective electrical signals responsive to presence of the first luminophore at the first polynucleotide (that is, incorporation of the first nucleic acid into the first polynucleotide) and responsive to presence of the second luminophore at the second polynucleotide (that is, incorporation of the second nucleic acid into the second polynucleotide).

Figure 10:
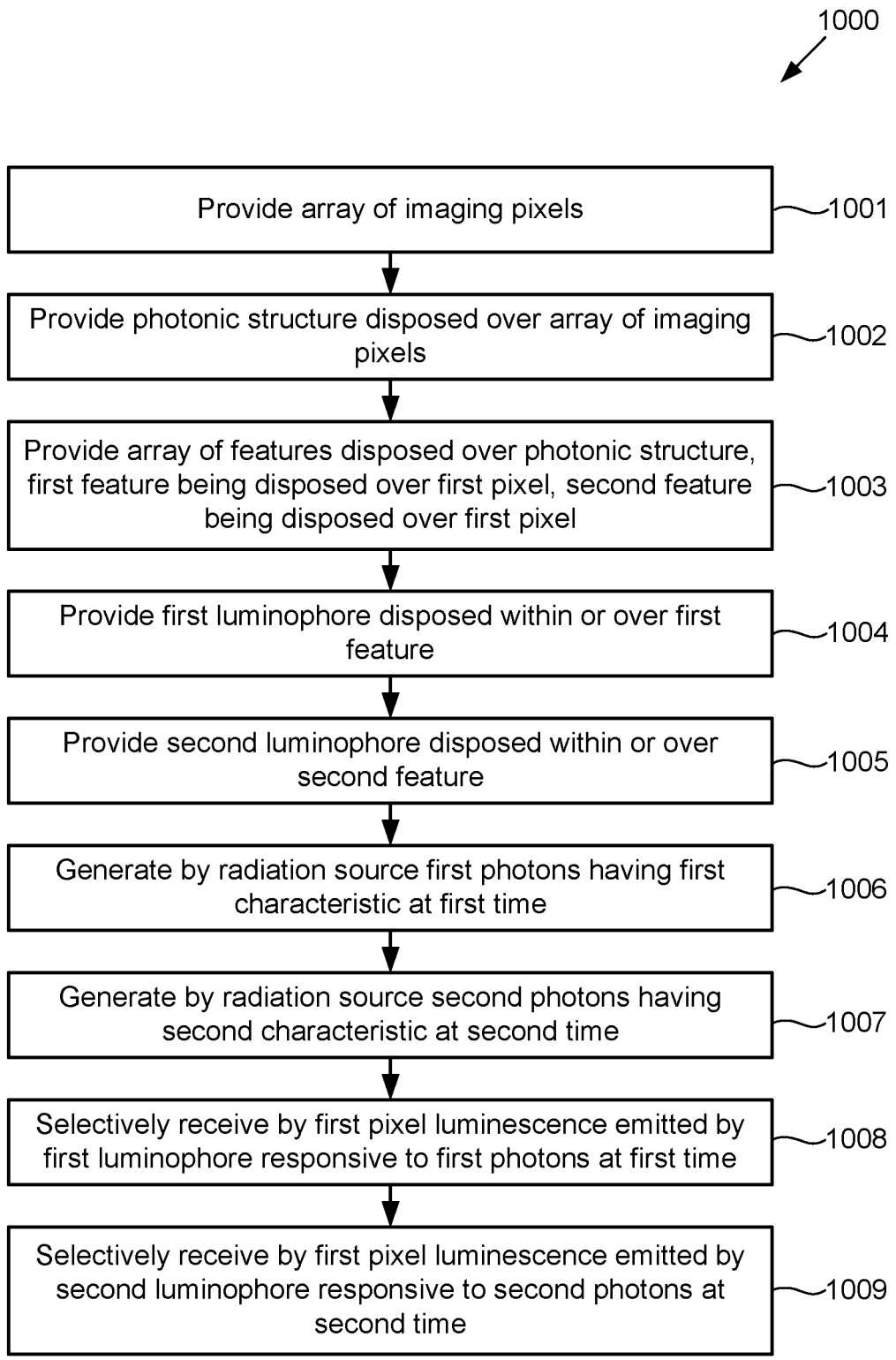
FIG. 10 illustrates an exemplary flow of steps in a method provided herein for use in luminescent imaging.

It should be appreciated that any suitable method can be used so as to image luminophores at multiple sites using a given pixel. For example, FIG. 10 illustrates an exemplary flow of steps in a method provided herein for use in luminescent imaging. Method 1000 illustrated in FIG. 10 can include providing an array of imaging pixels (1001). For example, arrays of imaging pixels are commercially available. Method 1000 illustrated in FIG. 10 also can include providing a photonic structure disposed over the array of imaging pixels (1002). For example, a photonic crystal, a photonic superlattice, a microcavity array, or an array of plasmonic nanoantennas can be disposed over the array of imaging pixels using any suitable combination of materials fabrication and patterning techniques such as known in the art.

Method 1000 illustrated in FIG. 10 also can include providing an array of features disposed over the photonic structure (1003). For example, an array of wells or posts can be disposed over the photonic structure using any suitable combination of materials fabrication and patterning techniques such as known in the art. The array of features can be registered with the photonic crystal and with the array of pixels such that an integer number n>2 of features is disposed over each pixel. For example, a first feature of the array of features can be disposed over a first pixel of the array of imaging pixels, and a second feature of the array of features can be disposed over the first pixel and spatially displaced from the first feature. For example, the second feature can be laterally displaced from the first feature. In one non-limiting example, the photonic structure includes a hexagonal lattice, and the imaging pixels are rectangular. The first and second features, e.g., the first and second posts or wells, optionally each can have a substantially circular cross-section. Optionally, the array of imaging pixels, the photonic structure, and the array of features can be monolithically integrated with one another, e.g., can be prepared as a unitary structure, such as using a sequence of CMOS processing steps.

Method 1000 illustrated in FIG. 10 also can include providing a first luminophore disposed within or over the first feature (1004), and providing a second luminophore disposed within or over the second feature (1005). For example, the array of features can include a plurality of wells. The first feature can include a first well within which the first luminophore is disposed, and the second feature can include a second well within which the second luminophore is disposed. As another example, the array of features can include a plurality of posts. The first feature can include a first post upon which the first luminophore is disposed, and the second feature can include a second post upon which the second luminophore is disposed. Optionally, the first and second luminophores respectively can be coupled directly or indirectly to the first and second features. As one nonlimiting example, the first and second luminophores respectively can be coupled to first and second nucleic acids and/or can be coupled to first and second polynucleotides being sequenced in a manner such as described elsewhere herein.

Method 1000 illustrated in FIG. 10 also can include generating by a radiation source first photons having a first characteristic at a first time (1006). The first photons having the first characteristic can generate a first resonant pattern within the photonic structure at the first time, the first resonant pattern selectively exciting the first luminophore relative to the second luminophore. Method 1000 illustrated in FIG. 10 generating by the radiation source second photons having a second characteristic at a second time (1007). The second characteristic can be different than the first characteristic, and the second time can be different than the first time. In one example, steps 1006 and 1007 respectively can include flood illuminating the photonic structure with the first and second photons and/or can include generating the first and second photons with a laser. Optionally, the first and second photons can be in the visible range of the spectrum and/or independently can have wavelengths between about 300 nm and about 800 nm.

The second photons having the second characteristic can generate a second resonant pattern within the photonic structure at the second time, the second resonant pattern selectively exciting the second luminophore relative to the first luminophore. Exemplary radiation sources, photon characteristics, and resonant patterns are described elsewhere herein. Illustratively, the first and second photon characteristics can be selected independently from the group consisting of wavelength, polarization, and angle. As one example, the first photon characteristic can include a first linear polarization, and the second photon characteristic can include a second linear polarization that is different than the first linear polarization. Optionally, the first linear polarization is substantially orthogonal to the second linear polarization. Alternatively, the first linear polarization can be rotated relative to the second linear polarization by between about 15 degrees and about 75 degrees. As another example, the first photon characteristic can include a first wavelength, and the second photon characteristic can include a second wavelength that is different than the first wavelength.

Optionally, the first and second photons each irradiate the photonic structure at substantially the same angle as one another. For example, the first and second photons each can irradiate the photonic structure at an angle approximately normal to a major surface of the photonic structure. Or, for example, the first and second photons each irradiate the photonic structure at an angle approximately parallel to a major surface of the photonic structure. In some embodiments, the radiation source can include an optical component, and method 1000 can further include controlling the optical component so as to impose the first characteristic on the first photons and configured to impose the second characteristic on the second photons. Illustratively, the optical component can include a birefringent material rotating the first photons to a first linear polarization responsive to a first control signal by a controller, and rotating the second photons to a second linear polarization responsive to a second control signal by the controller. Additionally, or alternatively, the optical component can control a wavelength or angle of the first and second photons responsive to control signals by the controller.

Method 1000 illustrated in FIG. 10 also can include selectively receiving by the first pixel luminescence emitted by the first luminophore responsive to the first photons at the first time (1008) and selectively receiving by the first pixel luminescence emitted by the second luminophore responsive to the second photons at the second time (1009). In a manner such as described elsewhere herein, the first pixel can generate respective electrical signals at the first and second times based upon which the first and second luminophores can be distinguished from one another.

Any suitable number of features can be disposed over the first pixel, e.g., three or four features in a manner such as described herein with reference to FIG. 3A-3B, 7A-7D, 8A8E, or 9A-9D. For example, a third feature of the array of features optionally can be disposed over the first pixel and spatially displaced from each of the first and second features, and method 1000 further can include providing a third luminophore disposed within or over the third feature; generating third photons having a third characteristic at a third time, the third characteristic being different than the first and second characteristics, the third time being different than the first and second times; and selectively receiving by the first pixel luminescence emitted by the third luminophore responsive to the third photons at the third time. Optionally, a fourth feature of the array of features can be disposed over the first pixel and spatially displaced from each of the first, second, and third features, and method 1000 further can include providing a fourth luminophore disposed within or over the fourth feature; generating fourth photons having a fourth characteristic at a fourth time, the fourth characteristic being different than the first, second, and third characteristics, the fourth time being different than the first, second, and third times; and selectively receiving by the first pixel luminescence emitted by the fourth luminophore responsive to the fourth photons at the fourth time. In one non-limiting example, the first luminophore can be coupled to a first nucleic acid, the second luminophore can be coupled to a second nucleic acid, the third luminophore can be coupled to a third nucleic acid, and the fourth luminophore can be coupled to a fourth nucleic acid.

Additionally, or alternatively, any suitable number of features can be disposed over a second pixel, e.g., two, three, four, or more than four features. For example, a third feature of the array of features can be disposed over a second pixel of the array of imaging pixels; a fourth feature of the array of features can be disposed over the second pixel and spatially displaced from the third feature; and method 1000 further can include providing a third luminophore disposed within or over the third feature; and providing a fourth luminophore disposed within or over the fourth feature. Method 1000 further can include selectively receiving by the second pixel luminescence emitted by the third luminophore responsive to the first photons at the first time or responsive to the second photons at the second time; and selectively receiving by the second pixel luminescence emitted by the fourth luminophore responsive to the first photons at the first time or responsive to the second photons at the second time. In one non-limiting example, the first luminophore can be coupled to a first nucleic acid, the second luminophore can be coupled to a second nucleic acid, the third luminophore can be coupled to a third nucleic acid, and the fourth luminophore can be coupled to a fourth nucleic acid.

Method 1000 can be adapted for luminescent imaging in an SBS scheme. For example, method 1000 can include providing at least one microfluidic feature in contact with the array of features and flowing, by the at least one microfluidic feature, one or more analytes to the first and second features. As another example, the first luminophore can be coupled to a first nucleotide, and the second luminophore can be coupled to a second nucleotide. Additionally, or alternatively, the first luminophore is coupled to a first polynucleotide to be sequenced, and the second luminophore can be coupled to a second polynucleotide to be sequenced. The first polynucleotide can be coupled to the first feature, and the second polynucleotide can be coupled to the second feature. Method 1000 further can include adding, by a first polymerase, a first nucleotide to a third polynucleotide that is complementary to and coupled to the first polynucleotide, the first nucleotide being coupled to the first luminophore. Method 1000 further can include adding, by a second polymerase, a second nucleotide to a fourth polynucleotide that is complementary to and coupled to the second polynucleotide, the second nucleotide being coupled to the second luminophore. Method 1000 further can include flowing, by a channel, a first liquid including the first and second nucleotides and the first and second polymerases into or over the first and second features.

Figure 11:
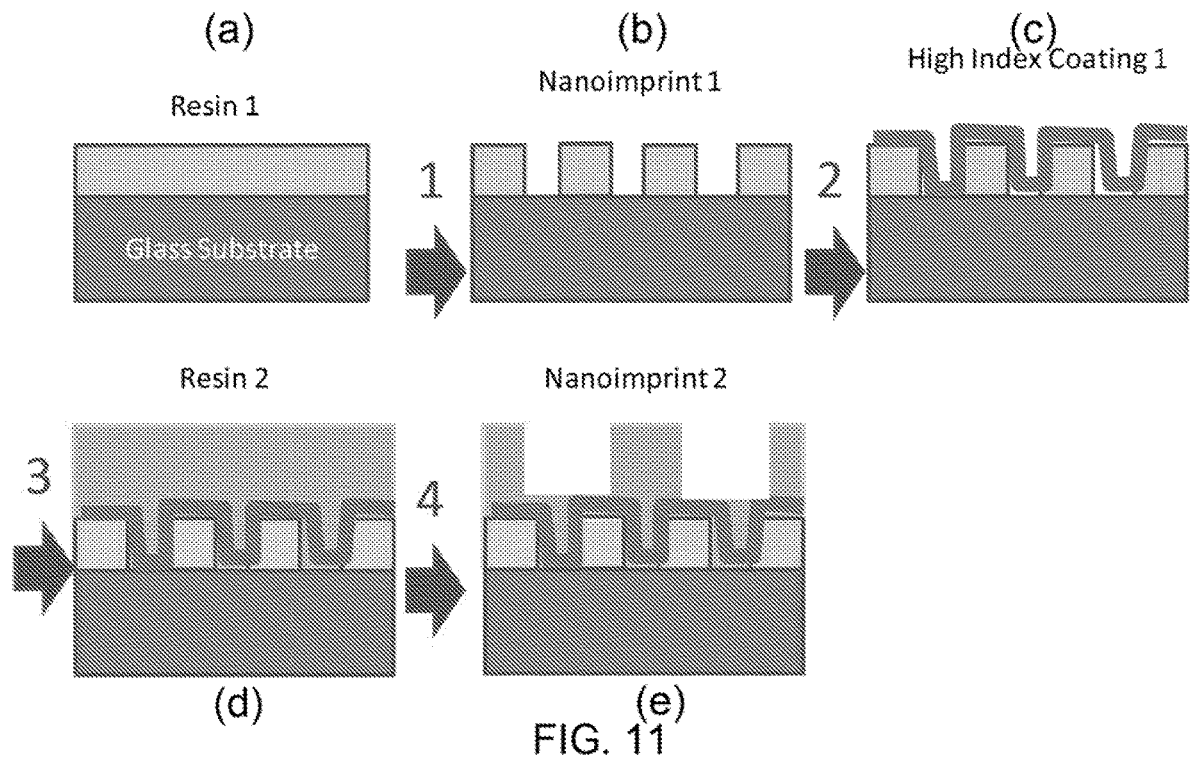
FIG. 11 illustrates an exemplary sequence of steps that can be used to prepare a device or composition such as provided herein.

As noted elsewhere herein, the present devices and methods can be prepared using any suitable combination of materials processing and patterning techniques. FIG. 11 illustrates an exemplary sequence of steps that can be used to prepare a device or composition such as provided herein. Illustratively, a device composition such as described herein with reference to FIGS. 3A-3B can be prepared using two nanoimprint lithography steps, followed by conformal dielectric deposition steps. For example, at step (a) of FIG. 11, a first, optically transparent material such as a dielectric or a semiconductor, e.g., a polymer (such as a resin), can be disposed over a substrate, e.g., a glass substrate. At step (b) of FIG. 11, the first material can be patterned using nanoimprint lithography, e.g., so as to define a plurality of features, such as wells or posts. At step (c) of FIG. 11, a third, optically transparent material, e.g., a dielectric or semiconductor material having a higher refractive index than the first material, can be disposed (e.g., conformally coated) over the features defined within the first material. At step (d) of FIG. 11, a fourth optically transparent material such as a dielectric or semiconductor, e.g., polymer (such as a resin) can be disposed over the third material. At step (e) of FIG. 11, the fourth material can be patterned using nanoimprint lithography, e.g., so as to define a plurality of wells or nanowells. The fourth material optionally fills spaces within the photonic structure, such as illustrated in FIG. 11(*e*). A second material (not specifically illustrated) that includes one or more luminophores can be disposed within the wells or nanowells, e.g., can be disposed over the photonic structure. Although FIG. 11 illustrates preparation of a single well per pixel, it should be understood that multiple wells per pixel readily can be prepared, e.g., by changing the distribution and size of features formed in the second nanoimprint step.

Figure 12:
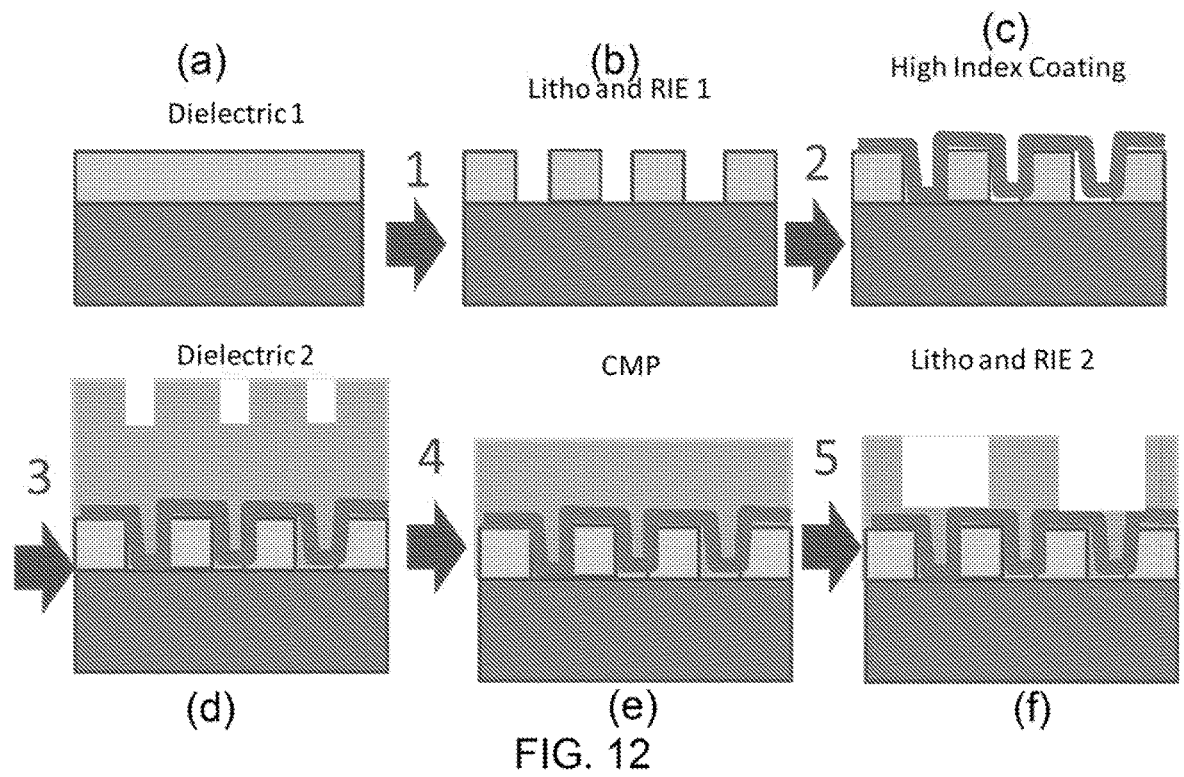
FIG. 12 illustrates an exemplary sequence of steps that can be used to prepare a device or composition such as provided herein.

As another example, a device or composition such as described herein with reference to FIGS. 3A-3B can be prepared using a combination of two photolithography steps, two RIE steps, a dielectric deposition and CMP. For example, FIG. 12 illustrates another exemplary sequence of steps that can be used to prepare a device or composition such as provided herein. At step (a) of FIG. 12, a first, optically transparent material such as a dielectric or a semiconductor, e.g., a polymer (such as a resin), can be disposed over a substrate, e.g., a glass substrate. At step (b) of FIG. 12, the first material can be patterned using photolithography followed by reactive ion etch (RIE), e.g., so as to define a plurality of features, such as wells or posts. At step (c) of FIG. 12, a third, optically transparent material, e.g., a dielectric or semiconductor material having a higher refractive index than the first material, can be disposed (e.g., conformally coated) over the features defined within the first material. At step (d) of FIG. 12, a fourth optically transparent material such as a dielectric or semiconductor, e.g., polymer (such as a resin) can be disposed over the third material. At step (e) of FIG. 12, the fourth material can be planarized, e.g., using chemical mechanical polishing (CMP). At step (f) of FIG. 12, the fourth material can be patterned using photolithography followed by RIE, e.g., so as to define a plurality of wells or nanowells. The fourth material optionally fills spaces within the photonic structure, such as illustrated in FIG. 12(*f*). A second material (not specifically illustrated) that includes one or more luminophores can be disposed within the wells or nanowells, e.g., can be disposed over the photonic structure. Although FIG. 12 illustrates preparation of a single well per pixel, it should be understood that multiple wells per pixel readily can be prepared, e.g., by changing the distribution and size of features formed in the second lithography and RIE steps.

Figure 13:
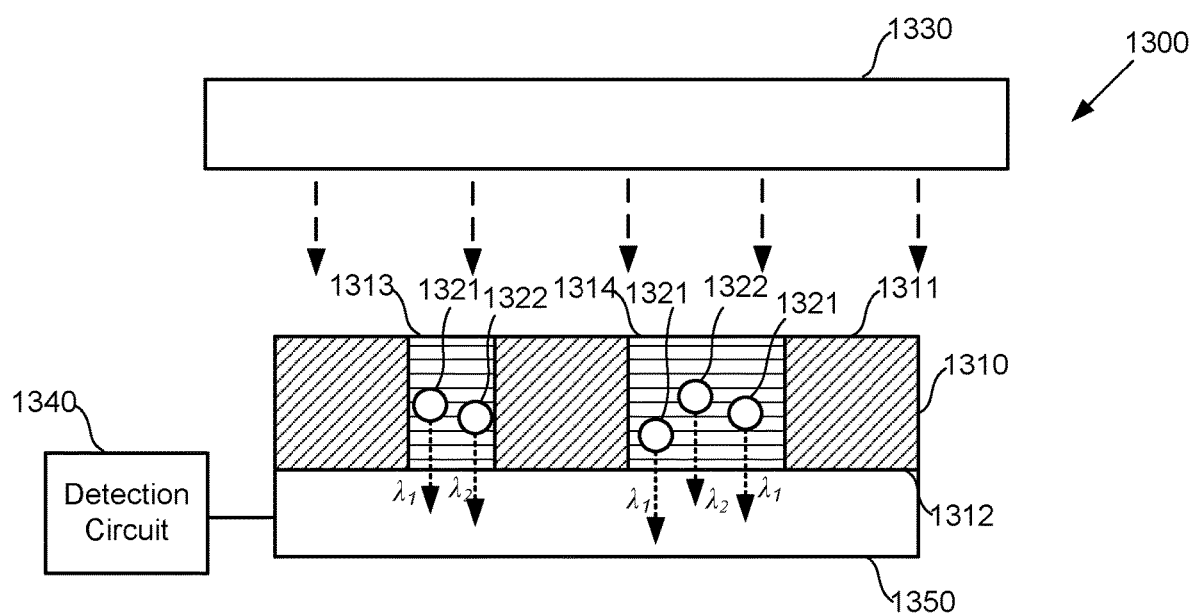
FIG. 13 illustrates an exemplary device for use in luminescent imaging such as provided herein.

It should be understood that the present devices suitably can be used in any of a variety of applications, e.g., for luminescent imaging. For example, FIG. 13 illustrates an exemplary device for use in luminescent imaging such as provided herein. FIG. 13 illustrates an exemplary device that includes photonic structure 1310, optical component 1330, imaging pixel 1350, and detection circuit 1340. Photonic structure 1310 includes a first material (indicated by diagonal pattern) having a first refractive index, and a second material (indicated by horizontally lined pattern) having a second refractive index that is different than the first refractive index. The first material can include first and second major surfaces 1311, 1312, and first and second pluralities of features, e.g., wells, 1313, 1314 defined through at least one of the first and second major surfaces. The features, e.g., wells, of the first plurality 1313 optionally can differ in at least one characteristic from the features, e.g., wells, of the second plurality 1314, e.g., can differ in shape, size, or distribution. For example, in the exemplary photonic structure 1310 illustrated in FIG. 13, the features, e.g., wells, of the first plurality 1313 optionally can differ in size (e.g., width) and in distribution (e.g., spacing) as compared to the features of the second plurality 1314. In the nonlimiting example illustrated in FIG. 13, the second material can be disposed within or between the first and second pluralities of features, e.g., wells, 1313, 1314 and can include first and second luminophores 1321, 1322. For example, some of first and second luminophores 1321, 1322 can be located within or between the first plurality of features, e.g., wells, 1313, and other of the first and second luminophores 1321, 1322 can be located within or between the second plurality of features, e.g., wells, 1314. In other embodiments such as discussed above with reference to FIGS. 3A-3B, the second material can be disposed over the first and second pluralities of features. Illustratively, the first material can include a polymer or a glass or other suitable material, or the second material can include a fluid or a gel or other suitable material. Optionally, photonic structure 1310 further includes a third material having a third refractive index that is different than the first and second refractive indices, the third material being disposed over at least one of the first and second pluralities of features, the second material being disposed over the third material, in a manner such as described herein with reference to FIGS. 3A-3B. Optionally, first luminophore 1321 can be coupled to a first nucleic acid, and second luminophore 1322 can be coupled to a second nucleic acid that is different than the first nucleic acid.

Photonic structure 1310 can selectively support a first resonant pattern responsive to irradiation with photons having a first characteristic at a first time, responsive to which first luminophore 1321 can emit first wavelength $\lambda_1$. Photonic structure 1310 can selectively support a second resonant pattern responsive to irradiation with photons having a second characteristic at a second time, responsive to which second luminophore 1322 can emit and second wavelength $\lambda_2$. The first and second wavelengths optionally can be different from one another, e.g., optionally can be separated from one another by a first non-propagating wavelength that does not selectively resonate within the photonic structure. Optical component 1330 can be disposed over one of the first and second major surfaces 1311, 1312 of the first material, e.g., over and optionally at a spaced distance from first major surface 1311. Optical component 1330 can be configured so as to irradiate photonic structure 1310 with the first photons at the first time and to irradiate photonic structure 1310 with the second photons at the second time. In the exemplary device illustrated in FIG. 13, the photonic structure 1310 is irradiated with the first and second photons at an angle approximately normal to first major surface 1311 of the first material, but it should be understood that any other angle, such as an angle disclosed herein, suitably can be used.

Photonic structure 1310 can be disposed over imaging pixel 1350, which can include an image sensor configured to image the received first and second wavelengths $\lambda_1$, $\lambda_2$ at the first and second times, respectively. Pixel 1350 can be spaced apart from photonic structure 1310, or can be in contact with photonic structure 1310, e.g., can be disposed in contact with second major surface 1312. Illustratively, pixel 1350 can include a complementary metal-oxide semiconductor (CMOS) based image sensor in contact with photonic structure 1310. Detection circuit 1340, which can be suitably electronically coupled to pixel 1350, can be configured so as to receive and analyze electrical signals from pixel 1350 at the first and second times. In a nonlimiting example in which the first and second luminophores respectively are coupled to first and second nucleic acids, detection circuit 1340 can be configured so as to identify, based on the electrical signals at the first and second times, which of the first and second nucleic acids have been to a particular polynucleotide that is coupled to the photonic structure, e.g., in a manner such as described elsewhere herein. Other imaging pixels, such as a pixel of a CCD camera, can be used. Exemplary detectors are set forth in Bentley et al., Nature 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405, 281, and US Pat. App. Publ. No. 2008/0108082, the entire contents of each of which is incorporated herein by reference.

Devices such as provided herein further can transmit radiation to the photonic structure so as suitably to excite luminophores therein. For example, device 1300 further can include a broadband excitation source, such as a light emitting diode (LED), or a narrowband excitation source, such as a laser, configured to generate radiation transmitted to the photonic structure by optical component 1330.

Note that the present devices, such as device 1300 illustrated in FIG. 13, optionally can include one or more microfluidic features such as described elsewhere herein. For example, device 1300 optionally can include at least one microfluidic feature in contact with the photonic structure and configured to provide a flow of one or more analytes into, between, or over the first and second pluralities of features disposed over the pixel. Such analytes optionally can include one or more reagents for nucleic acid sequencing such as nucleotides, nucleic acids or polymerases.

Thus, provided herein are devices, compositions, and methods including photonic structures that can provide single color or multicolor luminescence signal enhancement at a greater number of sites than the number of pixels used in luminescent imaging, e.g., are compatible with previously known epifluorescence microscopy scanning systems, such as sequencing platforms that are commercially available, e.g., from Illumina, Inc. For example, some embodiments of the present devices, compositions, and methods can create excitation "hotspots" separated by distances on the order of the wavelength of light. Spatial distribution of these high-intensity resonant features (e.g., Fano or guided mode resonances) can be tuned, for example, by appropriately selecting the photonic structure lattice features (e.g., symmetry) and/or the wavelength, angle, and or/polarization state of the excitation beam. Placing luminophores (e.g., biomolecules coupled to such luminophores) in proximity to such photonic structures can enhance luminescence signal but resonantly enhancing luminophore excitation, luminescence collection, or both. As such, photonic structures are an attractive platform for achieving luminescence signal enhancement from multiple imaging sites above single pixels, e.g., using uniform illumination, where selective imaging site excitation can be achieved by controlling the characteristics of the excitation beam at different times. The photonic structures can be tuned so as to reduce cross-talk terms such as described herein with reference to FIGS. 7D and 8E. Alternatively, the photonic structure can be omitted, and the excitation beam can be directed to selected ones of the imaging sites, e.g., using free space optics or multi-laser interference.

Other Alternative Embodiments

While various illustrative embodiments of the invention are described above, it will be apparent to one skilled in the art that various changes and modifications may be made therein without departing from the invention. For example, although certain compositions, systems, and methods are discussed above with reference to luminescent imaging associated with sequencing polynucleotides such as DNA or RNA, it should be understood that the present compositions, systems, and methods suitably can be adapted for use in luminescent imaging associated with any appropriate subject. The appended claims are intended to cover all such changes and modifications that fall within the true spirit and scope of the invention.

What is claimed:

1. A device for use in luminescent imaging, the device comprising:
    an array of imaging pixels;
    a photonic structure disposed over the array of imaging pixels;

an array of wells disposed over the photonic structure, the array of wells comprising:
- a first well corresponding to a first pixel of the array of imaging pixels, and
- a second well corresponding to the first pixel, the second well being spatially displaced from the first well;

a first luminophore disposed within the first well;
a second luminophore disposed within the second well;
a radiation source configured to generate first photons having a first characteristic, and configured to generate second photons having a second characteristic, the second characteristic being different than the first characteristic, wherein the first and second characteristics are selected independently from the group consisting of polarization, wavelength, and angle; and
a controller coupled to the radiation source and configured to cause the radiation source to illuminate the photonic structure with the first photons at a first time and to illuminate the photonic structure with the second photons at a second time which is different from the first time,
wherein the photonic structure causes the first photons to interfere with one another in such a manner as to selectively illuminate the first well, with a first interference pattern, the first interference pattern having a field strength that is more intense at the first well than at the second well and thus selectively excites the first luminophore to a greater extent than the second luminophore at the first time, and
wherein the photonic structure causes the second photons to interfere with one another in such a manner as to selectively illuminate the second well, with a second interference pattern, the second interference pattern having a field strength that is more intense at the second well than at the first well and thus excites the second luminophore to a greater extent than the first luminophore at the second time, the second interference pattern being different than the first interference pattern; and
wherein the first pixel is configured to receive luminescence emitted by the first luminophore of the first well responsive to the selective illumination of the first well by the first interference pattern at the first time, and is configured to receive luminescence emitted by the second luminophore of the second well responsive to selective illumination of the second well by the second interference pattern at the second time.

2. The device of claim 1, wherein the array of imaging pixels, the photonic structure, and the array of wells are monolithically integrated with one another.

3. The device of claim 1, wherein the photonic structure comprises a photonic crystal, a photonic superlattice, a microcavity array, or an array of plasmonic nanoantennas.

4. The device of claim 1, wherein the second well is laterally displaced from the first well.

5. The device of claim 1, wherein:
a third well of the array of wells corresponds to the first pixel and is spatially displaced from each of the first and second wells;
the device further comprises a third luminophore disposed within the third well;
the radiation source is configured to generate third photons having a third characteristic, the third characteristic being different than the first and second characteristics;
the controller is configured to cause the radiation source to illuminate the photonic structure with the third photons at a third time, the third time being different than the first and second times;
the photonic structure causes the third photons to interfere with one another in such a manner as to selectively illuminate the third well, with a third interference pattern, the third interference pattern having a field strength that is more intense at the third well than at the first and second wells and thus selectively excites the third luminophore to a greater extent than the first and second luminophores at the third time, the third interference pattern being different from the first and second interference patterns; and
the first pixel is configured to receive luminescence emitted by the third luminophore of the third well responsive to the selective illumination of the third well by the third interference pattern at the third time.

6. The device of claim 5, wherein:
a fourth well of the array of wells corresponds to the first pixel and is spatially displaced from each of the first, second, and third wells;
the device further comprises a fourth luminophore disposed within the fourth well;
the radiation source is configured to generate fourth photons having a fourth characteristic, the fourth characteristic being different than the first, second, and third characteristics;
the controller is configured to cause the radiation source to illuminate the photonic structure with the fourth photons at a fourth time, the fourth time being different than the first, second, and third times;
the photonic structure causes the fourth photons to interfere with one another in such a manner as to selectively illuminate the fourth well with a fourth interference pattern, the fourth interference pattern having a field strength that is more intense at the fourth well than at the first, second, and third wells and thus selectively excites the fourth luminophore to a greater extent than the first, second, and third luminophores at the fourth time, the fourth interference pattern being different from the first, second, and third interference patterns; and
the first pixel is configured to receive luminescence emitted by the fourth luminophore of the fourth well responsive to the selective illumination of the fourth well by the fourth interference pattern at the fourth time.

7. The device of claim 1, wherein:
a third well of the array of wells corresponds to a second pixel of the array of imaging pixels;
a fourth well of the array of wells corresponds to the second pixel and is spatially displaced from the first, second, and third wells;
the device further comprises a third luminophore disposed within the third well;
the device further comprises a fourth luminophore disposed within the fourth well;
the first interference pattern further selectively illuminates the third well, the first interference pattern having a field strength that is more intense at the third well than at the fourth well and thus selectively excites the third luminophore to a greater extent than the fourth luminophore at the first time;
the second interference pattern further selectively illuminates the fourth well, the second interference pattern having a field strength that is more intense at the fourth well than at the third well and thus selectively excites the fourth luminophore to a greater extent than the third luminophore at the second time;

the second pixel is configured to receive luminescence emitted by the third luminophore responsive to the selective illumination of the third well by the first interference pattern at the first time; and the second pixel is configured to receive luminescence emitted by the fourth luminophore responsive to the selective illumination of the fourth well by the second interference pattern at the second time.

8. The device of claim 1, wherein the photonic structure comprises a hexagonal lattice and wherein the imaging pixels are rectangular.

9. The device of claim 1, wherein the first and second photons independently have wavelengths between about 300 nm and about 800 nm.

10. The device of claim 1, wherein the first luminophore is coupled to a first nucleic acid, wherein the second luminophore is coupled to a second nucleic acid, wherein the first nucleic acid is coupled to a first polynucleotide to be sequenced, and wherein the second nucleic acid is coupled to a second polynucleotide to be sequenced.

11. A method for use in luminescent imaging, the method comprising:

at a first time, illuminating a photonic structure disposed over an array of imaging pixels with first photons from a radiation source, the first photons having a first characteristic;

causing, by the photonic structure, the first photons to interfere with one another in such a manner as to selectively illuminate a first well of an array of wells disposed over the photonic structure, with a first interference pattern, the first interference pattern having a field strength that is more intense at the first well than at a second well of the array of wells, the first well corresponding to a first pixel of the array of imaging pixels;

at a second time, illuminating the photonic structure with second photons from the radiation source, the second photons having a second characteristic, the second characteristic being different than the first characteristic, the second time being different than the first time, wherein the first and second characteristics are selected independently from the group consisting of polarization, wavelength, and angle;

causing, by the photonic structure, the second photons to interfere with one another in such a manner as to selectively illuminate the second well, with a second interference pattern, the second interference pattern having a field strength that is more intense at the second well than at the first well, the second well corresponding to the first pixel and spatially displaced from the first well, the second interference pattern being different than the first interference pattern;

receiving, by the first pixel, luminescence emitted by a first luminophore disposed within the first well responsive to the selective illumination of the first well by the first interference pattern at the first time; and receiving, by the first pixel, luminescence emitted by a second luminophore disposed within the second well responsive to the selective illumination of the second well by the second interference pattern at the second time.

12. The method of claim 11, wherein the photonic structure comprises a photonic crystal, a photonic superlattice, a microcavity array, or an array of plasmonic nanoantennas.

13. The method of claim 11, wherein the second well is laterally displaced from the first well.

14. The method of claim 11, wherein a third well of the array of wells corresponds to the first pixel and is spatially displaced from each of the first and second wells, and the method further comprises:

at a third time, illuminating the photonic structure with third photons from the radiation source, the third photons having a third characteristic, the third characteristic being different than the first and second characteristics, the third time being different than the first and second times;

causing, by the photonic structure, the third photons to interfere with one another in such a manner as to selectively illuminate the third well, with a third interference pattern, the third interference having a field strength that is more intense at the third wells than at the first and second wells, the third well being spatially displaced from the first and second wells, the third interference pattern being different than the first and second interference patterns; and receiving, by the first pixel, luminescence emitted by a third luminophore disposed within the third well responsive to the selective illumination of the third well by the third interference pattern at the third time.

15. The method of claim 11, wherein:

a third well of the array of wells corresponds to a second pixel of the array of imaging pixels;

a fourth well of the array of wells corresponds to the second pixel and is spatially displaced from the third well; and the method further comprises:

receiving, by the second pixel, luminescence emitted by a third luminophore disposed within the third well responsive to selective illumination of the third well by the first interference pattern at the first time; and receiving, by the second pixel, luminescence emitted by a fourth luminophore disposed within the fourth well responsive to selective illumination of the fourth well by the second interference pattern at the second time.

16. The method of claim 11, comprising flood illuminating the photonic structure with the first photons at the first time and with the second photons at the second time.

17. The method of claim 11, further comprising flowing one or more analytes to the first and second wells.

18. The device of claim 10, further comprising:

a third polynucleotide, the third polynucleotide being complementary to and coupled to the first polynucleotide;

a fourth polynucleotide, the fourth polynucleotide being complementary to and coupled to the second polynucleotide;

a first polymerase, the first polymerase being configured to add the first nucleic acid to the third polynucleotide, the first polynucleotide being coupled to the first well;

a second polymerase, the second polymerase being configured to add the second nucleic acid to the fourth polynucleotide, the second polynucleotide being coupled to the second well;

a liquid, the liquid comprising the first and second nucleic acids and the first and second polymerases; and a channel, the channel being configured to allow the liquid to flow through and into or over the first and second wells.

19. The method of claim 11, wherein the first luminophore is coupled to a first nucleic acid, wherein the second luminophore is coupled to a second nucleic acid, wherein the first nucleic acid is coupled to a first polynucleotide to be sequenced, and wherein the second nucleic acid is coupled to a second polynucleotide to be sequenced.

20. The device of claim 3, wherein the photonic structure comprises a photonic superlattice, the photonic superlattice supporting propagation of the first photons and the second photons, the photonic superlattice inhibiting propagation of third photons having a wavelength between the wavelength of the first photons and the wavelength of the second photons.

21. The device of claim 3, wherein the photonic structure comprises a photonic superlattice, the photonic superlattice comprising:
   a first material having a first refractive index, the first material comprising first and second major surfaces and first and second pluralities of wells defined through at least one of the first and second major surfaces, the wells of the first plurality differing in at least one characteristic from the wells of the second plurality; and
   a second material having a second refractive index that is different than the first refractive index, the second material being disposed within, between, or over the first and second pluralities of wells and comprising the first and second luminophores.

22. The method of claim 12, wherein the photonic structure comprises a photonic superlattice, the photonic superlattice supporting propagation of the first photons and the second photons, the photonic superlattice inhibiting propagation of third photons having a wavelength between the wavelength of the first photons and the wavelength of the second photons.

23. The method of claim 12, wherein the photonic structure comprises a photonic superlattice, the photonic superlattice comprising:
   a first material having a first refractive index, the first material comprising first and second major surfaces and first and second pluralities of wells defined through at least one of the first and second major surfaces, the wells of the first plurality differing in at least one characteristic from the wells of the second plurality; and
   a second material having a second refractive index that is different than the first refractive index, the second material being disposed within, between, or over the first and second pluralities of wells and comprising the first and second luminophores.

24. The method of claim 10, wherein the photonic structure comprises a hexagonal lattice and wherein the imaging pixels are rectangular.

25. The method of claim 19, further comprising:
   adding, by a first polymerase, a first nucleic acid to a third polynucleotide that is complementary to and coupled to the first polynucleotide, the first nucleic acid being coupled to the first luminophore, and the first polynucleotide being coupled to the first well;
   adding, by a second polymerase, a second nucleic acid to a fourth polynucleotide that is complementary to and coupled to the second polynucleotide, the second nucleic acid being coupled to the second luminophore, and the second polynucleotide being coupled to the second well; and
   flowing, by a channel, a liquid including the first and second nucleic acids and the first and second polymerases into or over the first and second wells.

* * * * *

UNITED STATES PATENT AND TRADEMARK OFFICE
CERTIFICATE OF CORRECTION

PATENT NO. : 11,579,336 B2
APPLICATION NO. : 16/093070
DATED : February 14, 2023
INVENTOR(S) : Topolancik et al.

It is certified that error appears in the above-identified patent and that said Letters Patent is hereby corrected as shown below:

In the Specification

On Column 35, Line 26, delete "well," and insert -- well --.

On Column 35, Line 34, delete "well," and insert -- well --.

On Column 36, Line 7, delete "well," and insert -- well --.

On Column 37, Line 33, delete "structure," and insert -- structure --.

On Column 37, Line 49, delete "well," and insert -- well --.

On Column 38, Line 15, delete "well," and insert -- well --.

Signed and Sealed this
Sixteenth Day of May, 2023

Katherine Kelly Vidal
*Director of the United States Patent and Trademark Office*